US006465246B1

(12) United States Patent
Mueller et al.

(10) Patent No.: US 6,465,246 B1
(45) Date of Patent: *Oct. 15, 2002

(54) ONCOGENE- OR VIRUS-CONTROLLED EXPRESSION SYSTEMS

(75) Inventors: Rolf Mueller; Hans-Harald Sedlacek, both of Marburg (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/196,099

(22) Filed: Nov. 20, 1998

(30) Foreign Application Priority Data

Nov. 21, 1997 (DE) .......................................... 197 51 587

(51) Int. Cl.⁷ ........................ C12N 15/09; C12N 15/85; C12N 15/00; C12P 21/06; C07H 21/04

(52) U.S. Cl. .................. 435/320.1; 435/69.7; 435/69.1; 435/91.4; 435/91.1; 435/325; 435/375; 530/352; 530/358; 536/23.4; 536/23.1; 536/23.5; 536/23.72

(58) Field of Search ............................. 435/320.1, 69.1, 435/91.1, 91.4, 455, 325, 375, 6, 69.7; 530/352, 358; 536/23.1, 23.4, 23.5, 23.72, 24.1

(56) References Cited

U.S. PATENT DOCUMENTS

| 5,464,758 A | 11/1995 | Gossen et al. ............. 435/69.1 |
| 5,561,119 A | 10/1996 | Jacquesy et al. | |
| 5,674,703 A | * 10/1997 | Woo et al. .................. 435/69.1 |
| 5,830,880 A | 11/1998 | Sedlacek et al. ............... 514/44 |
| 5,854,019 A | 12/1998 | Sedlacek et al. ............ 435/69.1 |
| 5,885,833 A | 3/1999 | Mueller et al. ............. 435/372 |
| 5,916,803 A | 6/1999 | Sedlacek et al. ......... 435/320.1 |

FOREIGN PATENT DOCUMENTS

| EP | 0 455 424 A2 | 11/1991 |
| EP | 0790313 | 8/1997 |
| EP | 0 926 237 A2 | 6/1999 |
| WO | 95/14777 | 6/1995 |
| WO | 95/16771 | 6/1995 |
| WO | 95/19367 | 6/1995 |
| WO | 96/01313 | 1/1996 |
| WO | 96/06938 | 3/1996 |
| WO | 96/06939 | 3/1996 |
| WO | 96/06940 | 3/1996 |
| WO | 96/06941 | 3/1996 |
| WO | 97/04092 | 2/1997 |
| WO | 97/12970 | 4/1997 |

OTHER PUBLICATIONS

Picard, D et al., A Movable and Regulable inactivation function within the steroid binding domain of the glucocorticoid receptor, Cell, vol. 54, pp. 1073–1080, Sep. 1988.*

Herman J. C. Berendsen, A Glimpse of the Holy Grail?, Science vol. 282, Oct. 23, 1998.*
Funk et al., *TIBS Trends In Biochemical Sciences* 23:337–341 (Sep. 1998).
Vidal et al., *Proc. Natl. Acad. Sci. USA* 93:10321–10326 (Sep. 1996).
Rivera et al., *Nature Medicine* 2:1028–1032 (Sep. 1996).
Kirchhoff et al., *Nucleic Acids Research* 21:2881–2889 (1993).
Wang et al., *Proc. Natl. Acad. Sci. USA* 91:8180–8184 (Aug. 1994).
Taya, *TIBS Trends in Biochemical Sciences* 22:14–17 (Jan. 1997).
Abarzua, Patricio et al., Microinjection of Monoclonal Antibody PAb421 into Human SW480 Colorectal Carcinoma Cells Restores the Transcription Activation Function to Mutant p53. *Cancer Research*, vol. 55; pp. 3490–3494 (1995).
Augustin–Voss, Hellmut G. et al., Migrating Endothelial Cells Are Distinctly Hyperglycosylated and Express Specific Migration–Associated Cell Surface Glycoproteins. *Journal of Cell Biology*, vol. 119(2); pp. 483–491 (1992).
Aulitzky et al., Interleukins: Clinical Pharmacology and Thereapeutic Use. *Drugs*, vol. 48; pp. 667–677 (1994).
Bauer, William R. et al., Twist and writhe of a DNA loop containing intrinsic bends. *Proc. Natl. Acad. Sci.*, vol. 90; pp. 833–837 (1993).
Berling, Barbara et al., Cloning of a Carcinoembryonic Antigen Gene Family Member Expressed in Leukocytes of Chronic Myeloid Leukemia Patients and Bone Marrow. *Cancer Research*, vol. 50; pp. 6534–6539 (1990).
Blackwood, Elizabeth M. et al., Max: A Helix–Loop–Helix Zipper Protein That Forms a Sequence–Specific DNA–Binding Complex with Myc. *Science*, vol. 251; pp. 1211–1217 (1991).
Bonsing, Bert A. et al., Specificity of Seven Monoclonal Antibodies Against p53 Evaluated With Western Blotting, Immunohistochemistry, Confocal Laser Scanning Microscopy, and Flow Cytometry.

(List continued on next page.)

*Primary Examiner*—David Guzo
*Assistant Examiner*—Gerald G. Leffers, Jr.
(74) *Attorney, Agent, or Firm*—Heller Ehrman White and McAuliffe

(57) ABSTRACT

Nucleic acid constructs for expressing an effector gene, with the nucleic acid construct comprising a promoter I (component a) which controls the expression of a transcription factor gene (component b), a transcription factor gene (component b), a promoter II (component c) to which the gene product of the transcription factor gene binds and which controls the expression of an effector gene (component d), and effector gene (component d), wherein the activity of the gene product of the transcription factor gene depends on one or more cellular regulatory proteins which bind to this gene product and affect its activity, and isolated cells containing the nucleic acid constructs, can be used for preparing a drug for treating diseases and in methods of treating diseases.

2 Claims, 1 Drawing Sheet

OTHER PUBLICATIONS

Borel, Franck et al., Effects of Denys–Drash Syndrome Point Mutations on the DNA Binding Activity of the Wilms' Tumor Suppressor Protein WT1. *Biochemistry*, vol. 35(37); pp. 12070–12076 (1996).

Boulikas, Teni, The phosphorylation connection to cancer (Review). *International Journal of Oncology*, vol. 6; pp. 271–278 (1995).

Brent, Roger et al., A Eukaryotic Transcriptional Activator Bearing the DNA Specificity of a Prokaryotic Repressor, *Cell*, vol. 43; pp. 729–736 (1985).

Brent, Roger et al., A bacterial repressor protein or a yeast transcriptional terminator can block upstream activation of a yeast gene. *Nature*, vol. 312; pp. 612–615 (1984).

Brown, Myles et al., lac Repressor Can Regulate Expression from a Hybrid SV40 Early Promoter Containing a *lac* Operator in Animal Cells. *Cell*, vol. 49; pp. 603–612 (1987).

Brown, Donald J. et al., Redundancy of Signal and Anchor Functions in the $NH_2$–Terminal Unchardged Region of Influenza Virus Neuraminidase, a Class II Membrane Glycoprotein. *Journal of Virology*, vol. 62(10); pp. 3824–3831 (1988).

Burrows, Francis J. et al., Vascular Targeting–A New Approach to the Therapy of Solid Tumors. *Pharmac. Ther.*, vol. 64; pp. 155–174 (1994).

Chasman, Daniel I. et al., GAL4 Protein: Purification, Association with GAL80 Protein, and Conserved Domain Structure. *Molecular and Cellular Biology*, vol. 10(6); pp. 2916–2923 (1990).

Cho, Yunje et al., Crystal Structure of a p53 Tumor Suppressor–DNA Complex: Understanding Tumorigenic Mutations. *Science*, vol. 265; pp. 346–355 (1994).

Christoffersen, Ralph E. et al., Ribozymes as Human Therapeutic Agents. *Journal of Medicinal Chemistry*, vol. 38(12); pp. 2023–2037 (1995).

Cosman, D. et al., Human macrophage Colony Stimulating Factor (M–CSF): Alternate RNA Splicing Generates Three Different Proteins that are Expressed on the Cell Surface and Secreted. *Behring Inst. Mitt.*, vol. 83; pp. 15–26 (1988).

Cotter, Thomas G. BCR–ABL: An Anti–Apoptosis Gene in Chronic Myelogenous Leukimia. *Leukemia and Lymphoma*, vol. 18; pp. 231–236 (1995).

Coustry, Francoise et al., Studies on Transcription Activation by the Multimeric CCAAT–binding Factor CBF. *Journal of Biological Chemistry*, vol. 270(1): pp. 468–475 (1995).

Crepieux, P. et al., The Ets Family of Proteins: Weak Modulators of Gene Expression in Quest for Transcriptional Partners. *Critical Reviews in Oncogenesis*, vol. 5(6); pp. 615–638 (1994).

Das, Gokul et al., Basal promoter elements as a selective determinant of transcriptional activator function. *Nature*, vol. 374; pp. 657–660 (1995).

Deonarain, M.P. et al., Targeting enzymes for cancer therapy; old enzymes in new roles. *British Journal Cancer*, vol. 70; pp. 786–794 (1994).

Courey, Albert J. et al., Analysis of Sp1 in Vivo Reveals Multiple Transcription Domains, Including a Novel Glutamine–Rich Activation Motif. *Cell*, vol. 55; pp. 887–898 (1988).

Dingermann, Theodor et al., RNA polymerase III catalysed transcription can be regulated in *Saccharomyces cerevisiae* by the bacterial tetracycline repressor–operator system. *EMBO*, vol. 11(4); pp. 1487–1492 (1992).

Dingwall, Colin et al., Nuclear targeting sequences–a–concensus? *TIBS*, vol. 16; pp. 478–481 (1991).

Dirks et al., Dicistronic transcription units for gene expression in mammalian cells. *Gene*, vol. 128; pp. 247–249 (1993).

Dorfman, David M. et al., Human Transcription Factor GATA–2. *Journal of Biological Chemistry*, vol. 267(2); pp. 1279–1285 (1992).

Drexler, Hans G. et al., Routine immunophenotyping of acute leukaemias. *Blut*, vol. 57; pp. 327–339 (1988).

Drexler, Hans G. et al., The use of monoclonal antibodies for the identification and classification of acute myeloid leukemias. *Leukemia Research*, vol. 10(3); pp. 279–290 (1986).

Dyson, Nicholas et al., The Human Papilloma Virus–16 E7 Oncoprotein Is Able to Bind to the Retinoblastoma Gene Product. *Science*, vol. 243; pp. 934–937 (1989).

Ellis, Ronald W. et al., Vaccine Development: Progression from Target Antigen to Product. *Genetically Engineered Vaccines*. Plenum Press, New York (1992).

Farrow, Stuart N. et al., Cloning of a bcl–2 homologue by interaction with adenovirus E1B 19K. *Nature*, vol. 374; pp. 731–733 (1995).

Ferguson, Michael A.J. et al., Cell–Surface Anchoring of Proteins Via Glycosyl–phosphatidylinositol Structures. *Ann. Rev. Biochem.*, vol. 58; pp. 285–320 (1988).

Fisher, F. et al., Transcription activation by Myc and Max: flanking sequences target activation to a subset of CACGTG motifs *in vivo*. *EMBO*, vol. 12(13); pp. 5075–5082 (1993).

Flemington, Erik K. et al., E2F–1–mediated transactivation is inhibited by complex formation with the retinoblastoma susceptibility gene product. *Product. Natl. Acad. Sci.*, vol. 90;pp. 6914–6918 (1993).

Freedman, Arnold S. et al., B–Cell Monoclonal Antibodies and Their Use in Clinical Oncology. *Cancer Investigation*, vol. 9(1); pp. 69–84 (1991).

Fuerst, Thomas R. et al., Transfer of the inducible *lac* repressor/operator system from *Escherichia coli* to a vaccinia virus expression vector. *Proc. Natl. Acad. Sci.*, vol. 86; pp. 2549–2553 (1989).

Gimble, Jeffrey M. et al., Activation of the Human Immunodeficiency Virus Long Terminal Repeat by Herpes Simplex Virus Type 1 Is Associated with Induction of a Nuclear Factor That Binds to the NF–kB/Core Enhancer Sequence. *Journal of Virology*, vol. 62(11); pp. 4104–4112 (1988).

Givol, David, The Minimal Antigen–Binding Fragment of Antibodies–Fv Fragment. *Molecular Immunology*, vol. 28(12); pp. 1379–1386 (1991).

Gossen, Manfred et al., Tight control of gene expression in mammalian cells by tetracycline–responsive promoters. *Proc. Natl. Acad. Sci.*, vol. 89; pp. 5547–5551 (1992).

Han, Jeonghoon et al., The E1B 19K protein blocks apoptosis by interacting with and inhibiting the p53 inducible and death–promoting Bax protein. *Genes & Development*, vol. 10; pp. 461–477 (1996).

Harris, Jonathan D. et al., Gene therapy for cancer using tumour–specific prodrug activation. *Gene Therapy*, vol. 1; pp. 170–175 (1994).

Hawkins, Robert E. et al., A Genetic Approach to Idiotype Vaccination. *Journal of Immunotherapy*, vol. 14; pp. 273–278 (1993).

Helin, Kristian et al., A cDNA Encoding a pRB–Binding Protein with Properties of the Transcription Factor E2F. *Cell*, vol. 70; pp. 337–350 (1992).

Hesketh, R., *The Oncogene Factsbook*. Academic Press; pp. 32–42 (1995).

Hodgson, Clague P. et al., Virosomes: Cationic Liposomes Enhance Retroviral Transduction. *Nature Biotechnology*, vol. 14; pp. 339–342 (1996).

Honn, Kenneth V. et al., Adhesion molecules and tumor cell interaction with endothelium and subendothelial matrix. *Cancer and Metastasis Review*, vol. 11; pp. 353–375 (1992).

Hoogenboom, H.R. et al., Building Antibodies from their genes. *Rev. Tr. Trans. Hemobiol.*, vol. 36; pp. 19–47 (1993).

Hu, Qianjin et al., Antibodies Specific for the Human Retinoblastoma Protein Identify a Family of Related Polypeptides. *Molecular and Cellular Biology*, vol. 11(11); pp. 5792–5799 (1991).

Hughes, Brenda J. et al., Monoclonal Antibody Targeting of Liposomes to Mouse Lung in Vivo. *Cancer Research*, vol. 49; pp. 6214–6220 (1989).

Hupp, T.R. et al., Regulation of the Specific DNA Binding Function of p53. *Cell*, vol. 71; pp. 875–886 (1992).

Huston, James S. et al., Medical Applications of Single–Chain Antibodies. *Int. Rev. Immunol.*, vol. 10; pp. 195–217 (1993).

Jannot, Christian B. et al., Characterization of scFv–421, a Single–Chain Antibody Targeted to p53. *Biochemical and Biophysical Res. Comm.*, vol. 230; pp. 242–246 (1997).

Kaufman, Randal J. et al., Improved vectors for stable expression of foreign genes in mammalian cells by use of the untranslated leader sequence from EMC virus. *Nucleic Acids Res.*, vol. 19(16);pp. 4485–4490 (1991).

Kern, Scott E. et al., Identification of p53 as a Sequence–Specific DNA–Binding Protein. *Science*, vol. 252; pp. 1708–1711 (1991).

Kim, Baek et al., Dimerization of a Specific DNA–Binding Protein on the DNA. *Science*, vol. 255; pp. 203–206 (1992).

Kristensen, Jergen S. Immunophenotyping in acute leukemia, myelodysplastic syndromes and hairy cell leukaemia. *Danish Medical Bulletin*, vol.) 41(1); pp. 52–65 (1994).

Lane, D.P. et al., T antigen is bound to a host protein in SV4O–transformed cells. *Nature*, vol. 278;pp. 261–263 (1979).

La Thangue, Nicholas B., DRTF1/E2F: an expanding family of heterodimeric transcription factors implicated in cell–cycle control. *TIBS*, vol. 19; pp. 108–114 (1994).

Legros, Yann et al., Linear antigenic sites defined by the B–cell response to human p53 are localized predominantly in the amino and carboxy–termini o fhte protein. *Oncogene*, vol. 9; pp. 2071–2076 (1994).

Li, Yun et al., The adenovirus E1A–associated 130kD protein is encoded by a member of the retinoblastoma gene family and physically interacts with cyclins A and E. *Genes & Development*, vol. 7; pp. 2366–2377 (1993).

Li, Xiao–Yan et al., Intron–Exon Organization of the NF–Y Genes: Tissue–Specific Splicing Modifies an Activation Domain. *Journal of Biological Chemistry*, vol. 267(13): pp. 8984–8990 (1992).

Lichtenstein, Drew L. et al. Definition and functional analysis of the signal/anchor domain of the human respiratory syncytial virus glycoprotein G. *Journal of General Virology*, vol. 77; pp. 109–188 (1996).

Lin, J. et al., Functions of the p53 Protein in Growth Regulation and Tumor Suppression. *Cold Spring Harbor Symposia on Quantitative Biology*, vol. LIX; pp. 215–223 (1994).

Lipton, Stuart A., Janus Faces of NF-$_k$B: Neurodestruction versus neuroprotection. *Nature Medicine*, vol. 3(1); pp. 20–22 (1997).

Liu, Yuan et al., ADP–ribosylation of *Rhizobium meliloti* Glutamine Synthetase III in Vivo. *Journal of Biological Chemistry*, vol. 270(4); pp. 1624–1628 (1995).

Lucibello, Frances C. et al., Periodic cdc25C transcription is mediated by a novel cell cycle–regulated repressor element (CDE). *EMBO*, vol. 14(1); pp. 132–142 (1995).

Maruyama, Kazuo et al., Lipid composition is important for highly efficient target binding and retention of immunoliposomes. *Proc. Natl. Acad. Sci. USA*, vol. 87; pp. 5744–5748 (1990).

Mermod, Nicolas et al., The Proline–Rich Transcriptional Activator of CTF/NF–1 is Distinct from the Replication and DNA Binding Domain. *Cell*, vol. 58; pp. 741–753 (1989).

Miller, Roger H. et al., HIV accessory proteins as therapy targets. *Nature Medicine*, vol. 3(4); pp. 389 394 (1997).

Moore, Malcolm A.S., Hematopoietic Reconstruction: New Approaches. *Clinical Cancer Research*, vol. 1; pp. 3–9 (1995).

Mountford, Peter S. et al., Internal ribosome entry sites and dicistronic RNAs in mammalian transgenesis. *Trends in Genetics*, vol. 11(5); pp. 179–184 (1995).

Morgan, Richard A. et al. Retroviral vectors containing putative internal ribosome entry sites: development of a polycistronic gene transfer system and applications to human gene therapy. *Nucleic Acids Research*, vol. 20(6); pp. 1293–1299 (1992).

Mullen, Craig A., Metabolic Suicide Genes in Gene Therapy. *Pharmac. Ther.*, vol. 63; pp. 199–207 (1994).

Naeim, Faramarz, Selection of Monoclonal Antibodies in the Diagnosis and Classification of Leukemias. *Dis. Markers*, vol. 7; pp. 1–14 (1989).

Nevins, Joseph R., E2F: A Link Between the Rb Tumor Suppressor Protein and Viral Oncoproteins. *Science*, vol. 258; pp. 424–429 (1992).

Nichols, Joni et al., Transcription Factors, Translocations, and Leukemia. *Blood*, vol. 80(12); pp. 2953–2963 (1992).

Nordeen, S.K., Luciferase Reporter Gene Vectors for Analysis of Promoters and Enhancers. *BioTechniques*, vol. 6(5); pp. 454–457 (1988).

Nozaki, Naohito et al., Immunoaffinity Purification and Characterization of CACGTG Sequence–Binding Proteins from Cultured Mammalian Cells Using an Anti c–Myc Monoclonal Antibody Recognizing the DNA–Binding Domain. *J. Biochem.*, vol. 121; pp. 550–559 (1997).

Oshima, Akihiro et al., Cloning, sequencing, and expression of cDNA for human α—glucuronidase. *Proc. Natl. Acad. Sci. USA*, vol. 84; pp. 685–689 (1987).

Ouellette, Michel M. et al., Complexes containing the retinoblastoma gene product recognize different DNA motifs related to the E2F binding site. *Oncogene*, vol. 7; pp. 1075–1081 (1992).

Park, Hae–Young et al., The Herpes Simplex Virus Thymidine Kinase Gene Promoter Contains a Novel Thyroid Hormone Response Element. *Mol. Endo.*, vol. 7(3); pp. 319–330 (1993).

Papavissiliou, Athanasios G. et al., Interaction of Cell and Virus Proteins with DNA Sequences Encompassing the Promoter/Regulatory and Leader Regions of the Herpes Simplex Virus Thymidine Kinase Gene. *Journal of Biological Chemistry*, vol. 265(16); pp. 9402–9412 (1990).

Pauli, Bendicht U. et al., Organ–preference of metastasis. *Cancer and Metastasis Reviews*, vol. 9; pp. 175–189 (1990).

Pawson, Tony, Protein modules and signalling networks. *Nature*, vol. 373; pp. 573–580 (1995).

Pelletier, Jerry et al., Internal initiation of translation of eukaryotic mRNA directed by a sequence derived from poliovirus RNA. *Nature*, vol. 334; pp. 320–325 (1988).

Pomerantz, Joel L. et al., Structure–Based Design of Transcription Factors. *Science*, vol. 267;pp. 93–96 (1995).

Riechmann, Lutz et al., Reshaping human antibodies for therapy. *Nature*, vol. 332; pp. 323–327 (1988).

Roggenbuck, Birgit et al., Human Papillomavirus Type 18 E6*, E6, and E7 Protein Synthesis in Cell–Free Translation Systems and Comparison of E6 and E7 In Vitro Translation Products to Proteins Immuno–Precipitated from Human Epithelial Cells. *Journal of Virology*, vol. 65(9); pp. 5068–5072 (1991).

Rong, Bing L. et al., HSV–1–Inducible Proteins Bind to NF—$_k$B—like Sites in the HSV–1 Genome. *Virology*, vol. 189; pp. 750–756 (1992).

Sarnow, Peter et al, Adenovirus E1b—58kd Tumor Antigen and SV40 Large Tumor Antigen Are Physically Associated with the Same 54 kd Cellular Protein in Transformed Cells. *Cell*, vol. 28; pp. 387–394 (1982).

Rosen, Craig A. et al., The Location of Cis—Acting Regulatory Sequences in the Human T Cell Lymphotropic Virus Type III (HTLV–III/LAV) Long Terminal Repeat. *Cell*, vol. 41; pp. 813–823 (1985).

Schranz, V., Monoclonal Antibodies: New Diagnostic and Therapeutic Means in Acute Leukaemias. *Therapia Hungarica*, vol. 38; pp. 3–12 (1990).

Schrewe, Heinrich et al., Cloning of the Complete Gene for Carcinoembryonic Antigen: Analysis of Its Promoter Indictates a Region Conveying Cell Typr—Specific Expression. *Molecular and Cellular Biology*, vol. 10(6); pp. 2738–2748 (1990).

Seipel, Katja et al., Different activation domains stimulate transcription from remote ('enhancer') and proximal ('promoter') positions. *EMBO*, vol. 11(13); pp. 4961–4968 (1992).

Simons, Annemarie et al., Possible ideal *lac* operator: *Escherichia coli lac* operator–like sequences from eukaryotic genomes lack the central G—C pair. *Proc. Natl. Acad. Sci. USA*, vol. 81;pp. 1624–1628 (1984).

Speir, Edith et al., Potential Role of Human Cytomegalovirus and p53 Interaction in Coronary Restenosis. *Science*, vol. 265; pp. 391–394 (1994).

Stickney, Dwight R. et al., Biologic response modifiers: therapeutic approaches to lymphoproliferative diseases. *Current Opin. Oncol.*, vol. 4; pp. 847–855 (1992).

Sugimoto, Yoshikazu et al., Efficient Expression of Drug-selectable Genes in Retroviral Vectors under Control of an Internal Ribosome Entry Site. *BioTechn.*, vol. 12; pp. 694–698 (1994).

Suzuki, Takeshi et al., Tax protein of HTLV–1 interacts with the Rel homology domain of NF—$_k$B p65 and c—Rel proteins bound to the NF—$_k$B binding site and activates transcription. *Oncogene*, vol. 9;pp. 3099–3105 (1994).

Szekely, Laszlo et al., EBNA–5, an Epstein–Barr virus–encoded nuclear antigen, binds to the retinoblastoma and p53 proteins. *Proc. Natl. Acad. Sci. USA*, vol. 90; pp. 5455–5459 (1993).

Tanaka, Masafumi et al., The Oct–2 Glutamine–Rich and Proline–Rich Activation Domains Can Synergize with Each Other or Duplicates of Themselves to Activate Transcription. *Molecular and Cellular Biology*, vol. 14(9); pp. 6046–6055 (1994).

Theodorakis, Paul et al., Unmasking of a proliferation–restraining activity of the anti–apoptosis protein EBV BHRH1. *Oncogene*, vol. 12; pp. 1707–1713 (1996).

Thomas, M.D. et al., A novel quantitative immunoassay system for p53 using antubodies selected for optimum designation of p53 status. *J. Clin. Pathol.*, vol. 50; pp. 143–147 (1997).

Triezenberg, Steven J., Structure and function of transcriptional activation domains. *Current Opinions in Genetics and Development*, vol. 5; pp. 190–196 (1995).

Triezenberg, Steven J. et al., Functional dissection of VP16, the *trans*—activator of herpes simplex virus immediate early gene expression. *Genes & Development*, vol. 2; pp. 718–729 (1988).

Truss, Mathias et al.k Steroid Hormone Receptors: Interaction with Deoxyribonucleic Acid and Transcription Factors. *Endocr. Review.*, vol. 14(4); pp. 459–479 (1993).

Urban, Manuela B. et al., The 65–kD subunit of NF—$_K$B is a receptor for for $l_KB$ and a modulator of DNA–binding specificity, *Genes & Development*, vol. 4; pp. 1974–1984 (1990).

Van Huijsduijnen, Rob Hooft et al., Co–evolution from yeast to mouse: cDNA cloning of the two NF—Y (CP—1/CBF) subunits. *EMBO*, vol. 9(10); pp. 3119–3127 (1990).

Van Kooten, Cees et al., Cytokines and Intracellular Signals Involved in the Regulation of B–CLL Proliferation. *Leukemia and Lymphoma*, vol. 12; pp. 27–33 (1993).

Varner, Judith A. et al., Review: The Integrin $\beta_v\alpha_3$= Angiogenesis and Apoptosis. *Cell Adhesion and Communication*, vol. 3; pp. 367–374 (1995).

Vijaya, S. et al., Transport to the Cell Surface of a Peptide Sequence Attached to the Truncated C Terminus of an N–Terminally Anchored Integral Membrane Protein. *Molecular and Cellular Biology*, vol. 8(4); pp. 1709–1714 (1988).

Walhout, A.J.M. et al. c–Myc/Max heterodimers bind cooperatively to the E–box sequences located in the first intron of the rat ornithine decarboxylase (ODC) gene. *Nucleic Acids Research*, vol. 25(8); pp. 1493–1501 (1997).

Werness, Bruce A. et al., Association of Human Papillomavirus Types 16 and 18 E6 Protiens with p53. *Science*, vol. 248; pp. 76–79 (1990).

Wang, Zhao–Yi et al., Products of alternately spliced transcripts of the Wilms' tumor suppressor gene, wt1, have altered DNA binding specificity and regulate transcription in different ways. *Oncogene*, vol. 10; pp. 415–422 (1995).

Wang, Xin Wei et al., Hepatitis B virus X protein inhibits p53 sequence–specific DNA binding, transcriptional activity, and association with transcription factor ERCC3. *Proc. Natl. Acad. Sci. USA*, vol. 91; pp. 2230–2234 (1994).

Westernick, M.A. Julie et al., Anti–idiotypic antibodies as vaccines against carbohydrates antigens. *Springer Seminars in Immunopathol.*, vol. 15; pp. 227–234 (1993).

Wilson, David B. et al., A Nonerythroid GATA–Binding Protein Is Required for Function of the Human Preproendothelin–1 Promoter in Endothelial Cells. *Molecular and Cellular Biology*, vol. 10(9); pp. 4854–4862 (1990).

Winter, Greg et al., Man–made antibodies. *Nature*, vol. 349; pp. 293–299 (1991).

Winter, Greg et al., Making Antibodies by Phage Display Technology. *Annu. Rev. Immunol.*, vol. 12; pp. 433 455 (1994).

Zimber–Strobl, Ursula et al., Epstein–Barr virus nuclear antigen 2 exerts its transactivating function through interaction with recombination signal binding protein RBP–$J_K$, the homologue of *Drosophila Suppressor of Hairless*. *EMBO*, vol. 13(20); pp. 4973–4982 (1994).

Zwicker, Jörk et al., Cell cycle regulation of the cyclin A, cdc25C and cdc2 genes is based on a common mechanism of transcriptional repression. *EMBO*, vol. 14(18); pp. 4514–4522 (1995).

Zwicker, Jörk et al., Cell cycle regulation of cdc25C transcription is mediated by the periodic repression of the glutamine–rich activators NF–y and Sp1. *Nucleic Acids Research*, vol. 23(19); pp. 3822–3830 (1995).

Zwicker, Jörk et al., Cell cycle–regulated transcription in mammalian cells. *Progress in Cell Cycle Research*, vol. 1; pp. 91–99 (1995).

\* cited by examiner

ONCOGENE- OR VIRUS-CONTROLLED EXPRESSION SYSTEMS

INFORMATION ON RELATED APPLICATIONS

The present application claims the priority benefit, under 35 U.S.C. §119, of Federal Republic of Germany Application No. 19751587.8, filed Nov. 21, 1997.

BACKGROUND OF THE INVENTION

1. Field of the Invention

The present invention relates to nucleic acid constructs for expressing an effector gene, methods of making such constructs, and methods of using such constructs.

2. Description of Related Art

A problem in gene therapy which is to a large extent inadequately solved is that of controlling the expression of an effector gene in a cell-specific manner, especially in diseased cells or cells which have otherwise been altered. The present invention comprises a novel process for achieving this control. The present invention is based on the finding (Werness et al., Science 248, 76 (1990)) that, in degenerate cells, regulatory proteins appear which are altered or diminished in such a way that they either are no longer able to bind to their affiliated partner molecules and interact with them, or they gain new binding properties with their affiliated partner molecules or with other partner molecules.

The novel process is furthermore based on the finding that the retinoblastoma protein, for example, is able to bind to the activation domain of the E2F transcription factor and thereby inhibit its activity (Flemington et al., PNAS USA 90, 69 14 (1993)).

Genes for regulatory proteins of this nature have already been used for expression systems for searching for inhibitors or stimulators of these regulatory proteins (e.g. WO95/19367, WO95/14777, WO97/04092).

In addition, vector systems with a first vector expressing a tumor suppressor protein and a second vector expressing a protein which binds to the tumor suppressor protein and thereby inhibits it, have already been disclosed (WO 95/16771). Both the vectors are introduced into one cell. By combining the two vectors, vectors encoding a tumor suppressor protein can be produced in the cell without the proliferation of the cell being inhibited by the tumor suppressor protein.

In addition, WO 97/12970 discloses expression systems in which the expression of a first gene is controlled by a first promoter whose function is suppressed in non-tumor cells, and the expression of a second gene, whose expression product inhibits the expression of the first gene in non-tumor cells, is controlled by a second promoter which is upregulated in non-tumor cells.

The present invention relates to a novel and simple expression system which can only be activated in cells in which such regulatory proteins occur in diminished or altered form. When activated, an effector gene which is encoded by the expression system is transcribed. The expression product of the effector gene has a prophylactic or therapeutic effect, either on its own or in combination with a further pharmaceutically active compound.

SUMMARY OF THE INVENTION

The present invention relates to a nucleic acid construct for expressing an effector gene. This nucleic acid construct comprises (a) a first promoter, (b) a transcription factor gene, the expression of which is controlled by the first promoter, (c) a second promoter, to which the gene product of the transcription factor gene binds, and (d) an effector gene, the expression of which is controlled by the second promoter, wherein the activity of the transcription factor gene product depends on one or more cellular regulatory proteins that bind to the transcription factor gene product and affect the activity thereof.

In one embodiment, the nucleic acid construct comprises (a) a first promoter comprising an activation sequence for the transcription of the transcription factor gene, (b) a transcription factor gene comprising (i) an activation domain, (ii) a binding sequence for a cellular regulatory protein, and (iii) a DNA-binding domain; (c) a second promoter comprising an activation sequence which is activated by binding the expression product of the transcription factor gene and activates the transcription of the effector gene, and (d) an effector gene.

In another embodiment of the invention, the nucleic acid construct comprises (a) a first promoter comprising an activation sequence for the transcription of the transcription factor gene comprising (i) a DNA-binding sequence for a cellular regulatory protein and (ii) a basal promoter; (b) a transcription factor gene comprising a gene encoding a repressor protein that inhibits the second promoter; (c) a second promoter comprising (i) an activation sequence for the transcription of the effector gene and (ii) a DNA sequence which binds the repressor protein and thereby inhibits the activation of the transcription of the effector gene; and (d) an effector gene.

The present invention also relates to vectors and isolated cells comprising the aforementioned nucleic acid construct. The vector may be a plasmid vector or a viral vector. The cell may be any cell, including mammalian cells.

The invention further relates to method of making the aforementioned nucleic acid construct comprising ligating the first promoter, transcription factor gene, second promoter, and effector gene together stepwise.

Still further, the present invention relates to methods of treating and/or preventing disease comprising administering to a patient the aforementioned nucleic acid construct or isolated cells containing the aforementioned nucleic acid construct. According to one aspect of the invention, the nucleic acid is administered to a patient externally, perorally, intravesically, nasally, intrabronchially or into the gastrointestinal tract, or injected into an organ, into a body cavity, into the musculature, subcutaneously or into the blood circulation. According to another aspect of the invention, the disease treated or prevented may be infections, tumors, leukemias, autoimmune diseases, allergies, arthritides, inflammations, organ rejections, graft versus host reactions, blood coagulation diseases, circulatory diseases, anemia, hormone diseases and CNS damage.

DETAILED DESCRIPTION OF THE INVENTION

1. General Description of the Invention

The present invention relates to a nucleic acid construct for expressing an effector gene, with the nucleic acid construct containing a first promoter (I) (component a) which controls the expression of a transcription factor gene (component b) which is likewise contained in the nucleic acid construct, and containing a second promoter (II) (component c) to which the gene product of the transcription factor gene binds specifically and which controls the expression of an effector gene (component d) which is likewise contained in the nucleic acid construct, wherein the activity of the gene product of the transcription factor gene depends on one or more cellular regulatory proteins which bind specifically to this gene product and affect its activity.

The expression system according to the invention is a nucleic acid construct whose expression is controlled by oncogenes or viruses, by means of these oncogenes or viruses altering or influencing regulatory proteins, and which, in the simplest case, contains the following components:

a) at least one activation sequence (promoter unit I)
b) at least one gene for a transcription factor, with its transcription being controlled by component a)
c) at least one further activation sequence (promoter unit II), which controls the expression of component d) by binding the transcription factor which is encoded by component b)
d) at least one effector gene.

Figure 1:
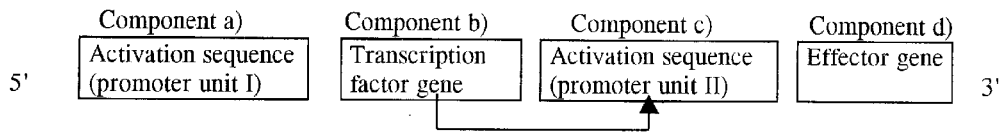
FIG. 1: Nature and arrangement of the general components of a nucleic acid construct of the present invention.

The arrangement of the individual components is depicted by way of example in FIG. 1.

In accordance with this invention, two particular embodiments of the nucleic acid construct, designated Embodiment A and Embodiment B, are to be distinguished.

Embodiment A)

This embodiment is characterized by the components having the following properties:

Component a)
  at least one activation sequence (promoter No. I);
Component b)
  at least one gene for a transcription factor, which comprises a fusion protein which contains:
    component $b_1$)—at least one activation domain of a transcription factor,
    component $b_2$)—at least one binding sequence of a binding protein for a regulatory protein, and
    component $b_3$)—at least one DNA-binding domain of a transcription factor;
Component c)
  at least one activation sequence (promoter No. II) which is activated by binding the transcription factor which is encoded by component b);
Component d)
  at least one effector gene.

Figure 2:
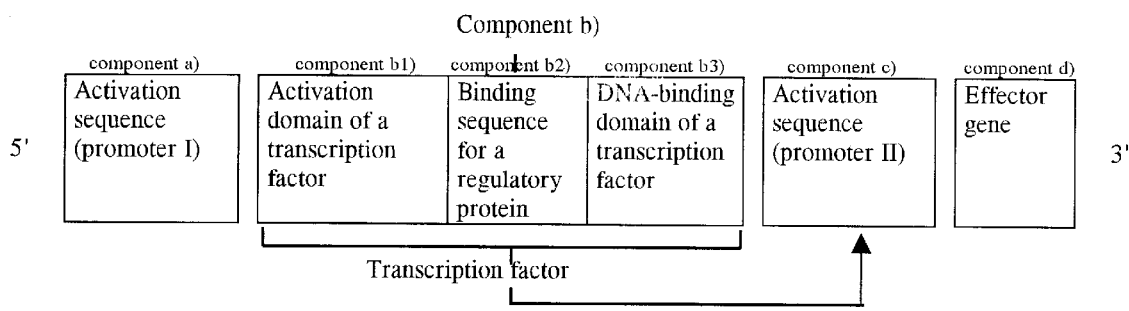
FIG. 2: Diagrammatic depiction of the arrangement of the general components of a nucleic acid construct in accordance with embodiment A of the invention.

The arrangement of the individual components is depicted by way of example in FIG. 2. A prerequisite for the functionality, according to the invention, of the expression system is that component $b_2$) is fitted between or onto components $b_1$) and $b_3$) such that the binding of the regulatory protein to component $b_2$) inhibits the functionality of the activation domain (component $b_1$) and/or the DNA-binding domain (component $b_3$). In normal cells, i.e. when the regulatory protein is capable of normal function, this inhibition leads to inhibition of the expression of the effector gene. In a degenerate or infected cell, in which the regulatory protein is either altered or complexed such that it is no longer able to interact with the affiliated binding protein, or is no longer present or is only present to a minor extent, this inhibition is lacking such that the transcription factor (component b) is able to activate the activation sequence (component c) in an unimpeded manner and thereby start transcription of the effector gene.

Transcription of the effector gene is initiated by the activation sequence [component a)] being activated, resulting in expression of the gene for the transcription factor [component b)]. The transcription factor [component b)] in turn binds to the activation sequence [component c)], which induces expression of the effector gene [component d)].

In a particular embodiment of this invention, component a) is the same as component c). In this special embodiment, a slight activation of the activation sequence [promoter I, component a)] leads to expression of the transcription factor [component b)], which activates both the activation sequence [promoter I, component a)] and the activation sequence [promoter II, component c)] and thereby both induces expression of the effector gene [component d)] and augments expression of the transcription factor [component b)], thereby once again augmenting expression of the effector gene [component d)].

Embodiment B)

This embodiment is characterized by the components having the following properties:

Component a')
  at least one activator sequence (promotor I), which contains:
    component $a_1$)—at least one DNA-binding sequence for a regulatory protein, and
    component $a_2$)—at least one basal promoter, with the binding of the regulatory protein to component al) activating component $a_2$);
Component b')
  at least one gene for a transcription factor which acts as a repressor, with its expression being induced by component a');
Component c')
  at least one activation sequence (promoter II), which contains:
    component $c_1$)—at least one activation sequence for inducing transcription of component d), and
    component $c_2$)—at least one DNA sequence for binding the repressor (component b'), with this binding inhibiting the activation of the transcription of the downstream effector gene (component d);
Component d)
  an effector gene.

Figure 3:
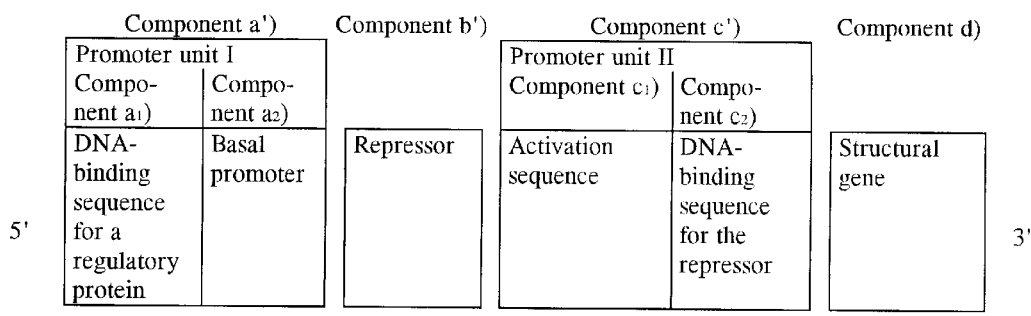
FIG. 3: Diagrammatic depiction of the arrangement of the general components of a nucleic acid construct in accordance with embodiment B of the invention.

The arrangement of the components of embodiment B) is depicted by way of example in FIG. 3.

A prerequisite for the expression system according to embodiment B) functioning in accordance with the invention is that, in the normal cell, the binding of a cellular regulatory protein to component a') of promoter unit I induces transcription of the repressor gene (component b') and that the expressed repressor binds to component $c_2$) of promoter unit II and thereby inhibits activation of the transcription of the structural gene (component d) by promoter unit II.

In a degenerate or infected cell, in which the regulatory protein is either altered or complexed such that it can no longer bind to the DNA-binding sequence (component $a_1$) in promoter unit I, or is no longer present or only present to a slight extent, there is no expression of the gene for the repressor and consequently no inhibition, either, of the expression of the novel nucleic acid construct.

In embodiment B) of the novel nucleic acid construct, transcription of the effector gene (component d) in these degenerate or infected cells is started by the activation sequence (component $c_1$) of promoter unit II being activated.

The expression system described by embodiments A) and B) can be extended by linking together several identical or different sequences for effector genes [component d), d'), d")], which are in each case linked to each other by identical or different IRES sequences or by activation sequences [components c') and c")].

This expression system can be extended in embodiment A) by linking together several identical or different genes for transcription factors [components b)], which are in each case linked to each other by identical or different IRES sequences or activation sequences [component a) or component c)].

When genes for different transcription factors are linked together, the activation sequences are to be selected such that they contain nucleotide sequences to which the transcription factor [components b)] is able to bind.

Depending on the choice of activation sequence [components a) or $c_1$)], the novel nucleic acid constructs can be used to express an effector gene [component d)] nonspecifically, cell-specifically or virus-specifically, or under particular metabolic conditions or cell cycle-specifically. The effector gene is a gene which, for its part, encodes a pharmacologically active compound or an enzyme which cleaves an inactive precursor of a drug into an active drug. For example, the effector gene can be selected such that this active compound or this enzyme is expressed together with a ligand as a fusion protein, and this ligand binds to the surface of cells, for example endothelial cells, tumor cells or leukocytes.

The novel nucleic acid constructs are preferably composed of DNA. The term "nucleic acid constructs" is understood to mean artificial structures which are composed of nucleic acid and which can be transcribed in the target cells.

The novel nucleic acid constructs are preferably inserted into a vector, with plasmid vectors or viral vectors being particularly preferred. Other suitable vectors into which the nucleic acid construct can be inserted will be know or apparent to those of skill in the art.

The nucleic acid construct, where appropriate inserted into a vector, is administered to a patient for the prophylaxis or therapy of a disease. The administration can be effected perorally, locally or by injection or infusion.

Viral or nonviral vectors may be used. For example viral vectors could be derived from RTV, AV, AAV or HSV (Jolly, Cancer Gene Ther. 1, 51 (1994)) or could be plasmids complexed with cationic lipids or cationic polymers (Ledley, Human Gene Ther. 6, 1129 (1995)). Such vectors might be solved in physiologic salt solutions containing 1% –30% human albumin (preferable 5%). $1 \times 10^5$–$1 \times 10^{10}$ PFU of viral vectors (preferable $1 \times 10^8$ PFU) or 0.01 mg–50 mg of plasmids (preferable 1 mg) are suspended in 1 ml of such a medium and applied to the patient. Application may be done by injection (i.v., i.a., s.c., i.m., into a cavity (pleura, peritoneum, subarachnoidal, into a joint) or into an organ or by local application (intrabronchial, intranasal, dermal, onto conjunctiva, intravaginal, into the bladder).

The present invention also relates to mammalian cells which contain a novel nucleic acid construct. In a particularly preferred embodiment, the nucleic acid constructs are introduced into cell lines which, after transfection, can then be used, as carriers of the novel expression system, for expressing the effector gene. Suitable cells will be know or apparent to those of skill in the art. In addition, suitable methods of introducing the nucleic acids constructs into suitable cells are will be known or apparent to those of skill in the art.

Such cells can be used for preparing a drug for patients. Alternatively, the cells or cell lines, such as tumor cells, immune cells or endothelial cells into which the novel nucleic acid constructs have been introduced, can be administered to patients locally or parenterally, for example intravenously, intraarterially, into a body cavity or into an organ, or be injected subcutaneously.

Examples of suitable cells or cell lines and their administration are tumor cells transduced in vitro and injected intradermally or subcutaneously for immunization of patients or CD4-positive T-cells transduced to express a new receptor for redirection of its cytotoxicity or muscle cells transduced in vitro to express F IX and reinjected for treatment of defective F IX production.

A preferred use of the novel nucleic acid construct consequently consists in the prophylaxis or treatment of a disease, with the invention comprising the in vitro insertion of a nucleic acid construct into a target cell, the nonspecific, virus-specific, target cell-specific, metabolically specific and/or cell cycle-specific expression of the drug in the target cell and the local or parenteral administration of the target cell to the patient, or else the local or parenteral administration of the nucleic acid construct to the patient for the in vivo insertion of a nucleic acid construct into the target cell.

The novel nucleic acid constructs do not occur in this form in nature, i.e. the effector gene for the active compound or for an enzyme or for a ligand-active compound or ligand-enzyme fusion protein is not naturally combined with nucleic acid sequences as contained in the novel nucleic acid construct.

Preferred effector genes, which are incorporated into an expression system according to the invention, encode a pharmacologically active compound. This active compound may be a protein or glycoprotein. Suitable proteins and glycoproteins are, for example, cytokines, growth factors, receptors for cytokines or growth factors, antibodies or antibody fragments, proteins having an antiproliferative or cytostatic effect, proteins having an apoptotic or antiapoptotic effect, tumor antigens, angiogenesis inhibitors, thrombosis-inducing proteins, coagulation inhibitors, proteins having a fibrinolytic effect, blood plasma proteins, complement-activating proteins, envelope substances of viruses and bacteria, hormones, peptides having an effect on the circulation, neuropeptides, enzymes, mediators, naturally occurring, unaltered regulatory proteins and ribozymes, or (antisense) ribonucleotides which have an inhibitory effect on gene expression.

The transgene is preferably an effector gene which encodes a ribozyme which inactivates the mRNA which encodes a protein which is selected from the group consisting of cell cycle control proteins, in particular cyclin A, cyclin B, cyclin D1, cyclin E, E2F1-5, cdc2, cdc25C or DP1, or viral proteins or cytokines or growth factors or their receptors.

In a further embodiment, the effector gene can encode a ligand-active compound fusion protein, with it being possible for the ligand to be an antibody, an antibody fragment, a cytokine, a growth factor, an adhesion molecule or a peptide hormone and the active compound to be a pharmacologically active compound, as described above, or an enzyme. For example, the effector gene can encode a ligand-enzyme fusion protein, with the enzyme cleaving a precursor of a drug into a drug and the ligand binding to a cell surface, preferably to endothelial cells or tumor cells.

III. Features of Embodiment A)
1) Component b)
1.1) Binding Sequence for a Regulatory Protein [Component $b_2$)]

A large number of cellular binding proteins for regulatory proteins have already been described [Zwicker and Müller, *Progress in Cell Cycle Res.* 1: 91 (1995); Boulikas et al., *Int. J. Oncol.* 6: 271 (1995); Pawson, *Nature* 373: 573 (1995); Cotter, *Leuk. Lymph.* 18: 231 (1995); Hesketh, *Oncogene Facts Book,* Acad. Press, ISBN 0-12-344550-7 (1995); Miller and Sarver, *Nature Med.* 3: 389 (1997)].

Binding proteins or their binding sequences which are suitable within the meaning of the invention are, in particular, binding proteins or their binding sequences for those regulatory proteins which are only expressed to a slight extent in diseased cells, whose binding to the binding sequence is inhibited, which are not present, or only present to a trivial extent, in free form due to an excess of binding sequence, or whose function is otherwise impaired or altered, for example by mutation.

These regulatory proteins include, for example, the proteins which are expressed by tumor suppressor genes.

A selection, which does not limit the invention, of regulatory proteins of this nature, and their affiliated binding proteins and the binding sequences of the latter, are listed in the following examples:

| Regulatory protein | Component $b_2$) (cellular binding protein having a binding sequence for the regulatory protein) |
|---|---|
| p53 | MDM-2 |
| pRb | Transcription factor E2F, -1, -2, -3 |
|  | Cyclin-$D_1$, $D_2$, -$D_3$, or -C |
|  | Cyclin-A, -E |
|  | Transcription factor PU.1 |
|  | Transcription factor Elf-1 |
| p130 | Transcription factor E2F-5 |
|  | Cyclin A, - E |
| Max | Myc |
| MAD | Myc |
| VHL | Elongin C, - B |
| cdk4 | p14, p15, p16, p18, p27, p57, p21 |
| MTS-1 (p16) | cdk4 |
| WT-1 | p53 |
| SMAD2 (MADR2) | DPC4 |
| DPC-4 | SMAD2 |
| β-catenin | LEF-1 |
| LEF-1 | β-catenin |

In a particular embodiment of this invention, component $b_2$) is a binding sequence of a non-cell-specific binding protein for a regulatory protein. Such a non-cell-specific binding sequence can, for example, be of viral, bacterial or parasitic origin.

The use of such a non-cell-specific binding sequence makes it possible for the function of component b) to be inhibited in normal cells by the affiliated regulatory protein being bound to component $b_2$). In infected cells, however, the affiliated regulatory protein is to a large extent bound as a result of the respective infectious agent producing the binding sequence-containing binding protein intracellularly. Component b) is therefore free and functional in these cells.

In another special embodiment of this invention, component $b_2$) is an antibody or a part of an antibody having binding sequences ($V_H$ and $V_L$) for a regulatory protein.

A selection, which does not limit the invention, of non-cell-specific binding sequences is listed in the following examples:

| Regulatory protein | Component $b_2$) (viral binding protein having a binding sequence for the regulatory protein) |
|---|---|
| p53 | IE 84 of CMV |
|  | (Speir et al., Science 265, 391 (1994)) |
|  | E1B (55 Kd) of AV |
|  | (Sarnow et al., Cell 28, 387 (1982); Lin et al., Cold Spring Harbor Symp. On Quantitative Biol. LIX, 215 (1995)) |
|  | EBNA-5 of EBV |
|  | (Szekely et al., PNAs USA 90, 5455 (1993)) |
|  | BHFR1 of EBV |
|  | (Theodorakis et al., Oncogene 12, 1707 (1996)) |
|  | E6 of HPV-16 or -18 |
|  | (Dyson et al., Science 243, 934 (1989); Howes et al., Genes Dev. 8, 1300 (1994)) |
|  | HBX protein of HBV |
|  | (Wang et al., PNAS USA 91, 2230 (1994)) |
|  | T antigen of SV40 |
|  | (Lane et al., Nature 278, 261 (1979); Linzer et al., Cell 17, 43 (1979)) |
| PRb | E1A of AV |
|  | (Nevins Science 258, 424 (1992)) |
|  | EBNA-2 of EBV |
|  | EBNA-1 or -5 of EBV |
|  | E7 of HPV |
|  | T antigen of SV40 |
| p130 | E1A of AV |
|  | (Li et al., Genes Dev. 7, 2366 (1993)) |
| CBF-1 (RBP-JK) | EBNA-2 of EBV |
|  | (Zimber-Strobl et al., EMBO J. 13, 4973 (1994)) |
| NF-Kappa B | Tax of HIV |
|  | (Suzuki et al., Oncogene 9, 3099 (1994)) |
| Lyn-tyrosine kinase | LMP-1 of EBV |
|  | LMP-2A or LMP-2B of EBV |
| Bak | E1B (16 Kd) of AV |
|  | (Farrow et al., Nature 374, 731 (1995)) |
| Bax | E1B (19 kD) of Av |
|  | (Han et al., Genes Dev. 10, 461 (1996)) |

| Regulatory protein | Antibodies or antibody fragments having a binding sequence ($V_H$, $V_L$) for the regulatory protein |
|---|---|
| p53 | monoclonal antibodies which are specific for the non-mutated DNA binding domain (Legros et al., Oncogene 9, 2071 (1994); 9, 3689 (1994); Hupp et al., Cell 71, 875 (1992); Abarzúa et al., Cancer Res. 55, 3490 (1995); Bonsing et al., Cytometry 28, 11 (1997); Thomas et al., J. Clin. Path. 50, 143 (1997); Jannot et al., BBRC 230, 242 (1997)) |
| PRb | monoclonal antibodies which are specific for active (non-phosphorylated) pRb (Hu et al., Mol. Cell Biol. 11, 5792 (1991)) |

When antibody is selected, the epitope-binding parts, $FV_L$, $FV_H$, of the antibody are preferably to be employed as component $b_2$), with this being in humanized form if they are of murine origin. The humanization is effected in a manner described by Winter et al., *Nature* 349: 293 (1991) and Hoogenbooms et al., *Rev. Tr. Transfus. Hemobiol.*, 36: 19 (1993). The antibody fragments are prepared in accordance with the state of the art, for example in the manner described by Winter et al., *Nature* 349, 293 (1991), Hoogenboom et al., *Rev. Tr. Transfus. Hemobiol.*, 36: 19 (1993), Givol, *Mol. Immunol.* 28: 1379 (1991) or Huston et al., *Int. Rev. Immunol.* 10: 195 (1993). The preparation of antibodies, antibody fragments and recombinant antibody fragments is described in detail in German Patent Application 196 49 645.4.

Recombinant antibody fragments are prepared directly from existing hybridomas or isolated from libraries of murine or human antibody fragments using "phage display" technology (Winter et al., *Annu. Rev. Immunol.* 12: 433 (1994)). These antibody fragments are then employed directly at the genetic level for coupling with components $b_1$) and $b_3$).

In order to prepare recombinant antibody fragments from hybridomas, the genetic information which encodes the antigen-binding domains ($V_H$, $V_L$) of the antibodies is obtained by isolating the mRNA, reverse transcribing the RNA into cDNA and subsequently amplifying by means of the polymerase chain reaction and oligonucleotides which are complementary to the 5'- and 3' ends, respectively, of the variable fragments. The resulting DNA fragments, encoding the $V_H$ and $V_L$ fragments, are then cloned into bacterial expression vectors, thereby making it possible to express, for example, Fv fragments, single-chain Fv fragments (scFv) or Fab fragments.

New antibody fragments can also be isolated directly from antibody libraries (immune libraries, native libraries) of murine or human origin using "phage display" technology. In the phage display of antibody fragments, the genes of antigen-binding domains are cloned, as gene fusions with the gene for the g3P coat protein of filamentous bacteriophages, either into the phage genome or into phagemid vectors in the form of scFv fragment genes or as Fab fragment genes. Antigen-binding phages are selected on antigen-loaded plastic vessels (panning), on antigen-conjugated paramagnetic "beads" or by binding to cell surfaces.

Immune libraries are prepared by subjecting the genes for the variable antibody fragments from B lymphocytes of immunized animals or patients to PCR amplification. For this, use is made of combinations of oligonucleotides which are specific for murine or human immunoglobulins or for the human immunoglobulin gene families.

Native libraries can be prepared by using non-immunized donors as the source of the immunoglobulin genes. Alternatively, immunoglobulin germline genes can be employed for preparing semisynthetic antibody repertoires, with the complementarity-determining region 3 of the variable fragments being amplified by PCR using degenerate primers. These so-called single-pot libraries have the advantage, as compared with immune libraries, that antibody fragments against a large number of antigens can be isolated from one single library.

The affinity of antibody fragments can be increased further by means of the phage display technology, with new libraries being prepared from already existing antibody fragments by means of random, codon-based or site-directed mutagenesis, by shuffling the chains of individual domains with those of fragments from naive repertoires, or by using bacterial mutator strains, and antibody fragments having improved properties being isolated by reselection under stringent conditions. In addition, murine antibody fragments can be humanized by the step-wise replacement of one of the variable domains with a human repertoire and subsequent selection using the original antigen ("guided selection"). Alternatively, murine antibodies are humanized by the targeted replacement of the hypervariable regions of human antibodies with the corresponding regions of the original murine antibody.

1.2) The Activation Domain [Component b1)] and the DNA-binding Domain [Component b3)]

Within the meaning of the invention, all available genes for activation domains and DNA-binding domains of a transcription factor can be used for component b). Examples, whose description is not, however, intended to limit the invention, are:

activation domains [component $b_1$)]at least one sequence
- of the cDNA for the acid transactivation domain (TAD) of HSV1-VP16 (amino acids 406 to 488; Triezenberg et al., *Genes Developm.* 2: 718 (1988); Triezenberg, *Curr. Opin. Gen. Developm.* 5: 190 (1995) or amino acids 413 to 490; Regier et al., *Proc. Natl. Acad. Sci. USA* 90, 883 (1993)) or
- of the activation domain of October 2 (amino acids 438 to 479; Tanaka et al., *Mol. Cell. Biol.* 14: 6046 (1994) or amino acids 3 to 154; Das et al., *Nature* 374: 657 (1995)) or
- of the activation domain of SP1 (amino acids 340 to 485; Courey and Tijan, *Cell* 55, 887 (1988)) or
- of the activation domain of NFY (amino acids 1 to 233; Li et al., *J. Biol. Chem.* 267: 8984 (1992); van Hujisduijnen et al., *EMBO J.* 9: 3119 (1990); Sinha et al., *J. Biol. Chem.* 92, 1624 (1995); Coustry et al. *J. Biol. Chem.* 270, 468 (1995)) or
- of the activation domain of ITF2 (amino acids 2 to 452; Seipel et al., *EMBO J.* 13, 4961, 1992)) or
- of the activation domain of c-Myc (amino acids 1 to 262; Eilers et al.) or
- of the activation domain of CTF (amino acids 399 to 499; Mermod et al., *Cell* 58, 741 (1989); Das and Herr, *Nature* 374, 657 (1995))

DNA-binding domains [component $b_3$)]at least one sequence
- of the cDNA for the DNA-binding domain of the Gal4 protein (amino acids 1 to 147; Chasman and Kornberg, *Mol. Cell. Biol.* 10: 2916 (1990)) or
- of the LexA protein (amino acids 1 to 81; Kim et al., *Science* 255: 203 (1992) or the whole LexA protein (amino acids 1 to 202; Brent et al., *Cell* 43: 729 (1985)) or
- of the lac repressor (lac I) protein (Brown et al., *Cell* 49: 603 (1987);

Fuerst et al., *PNAS USA* 86: 2549 (1989)) or
- of the tetracycline repressor(tet R) protein (Gossen et al., *PNAS USA* 89; 5547 (1992); Dingermann et al., *EMBO J.* 11: 1487 (1992)) or
- of the ZFHD1 protein (Pomerantz et al., *Science* 267: 93 (1995)).

Within the meaning of the invention, it is advantageous to add a nuclear localization signal (NLS) to the 3' end of the DNA-binding domain.

2) The Activation Sequence Promoter Unit II [Component c)] Which Can be Activated by Component b)

The choice of this activation sequence depends on the choice of the DNA-binding domain [component $b_3$)] in the gene for a transcription factor [component b)]. The following possibilities in turn exist, by way of example, for the examples of DNA-binding domains which were listed under 1.2:

2.1) Possibility A)
an activation sequence containing at least one binding sequence [nucleotide sequence: 5'-CGGACAACTGTT GACCG-3'] (SEQ ID NO.: 1) for the Gal4 protein (Chasman and Kornberg, *Mol. Cell Biol.* 10: 2916 (1990)) and (to whose 3' end) is added
- the basal promoter of SV40 (Nucleotides 48 to 5191; Tooze (ed), DNA Tumor Viruses (Cold Spring Harbor New York, N.Y.; Cold Spring Harbor Laboratory) or
- the promoter of c-fos (Das et al., *Nature* 374, 657 (1995)) or
- the U2 sn RNA promoter or
- the promoter of HSV TK (Papavassiliou et al., *J. Biol. Chem.* 265, 9402 (1990); Park et al., *Molec. Endocrinol.* 7, 319 (1993)).

2.2) Possibility B)
an activation sequence
containing at least one binding sequence [nucleotide sequence 5'-TACTGTATGTACA TACAGTA-3'] (SEQ ID NO.: 2) for the LexA protein [LexA operator; Brent et al., Nature 612, 312 (1984)] and (to whose 3' end) is added
the basal promoter of SV40 (nucleotides 48 to 5191; Tooze (ed), DNA Tumor Viruses (Cold Spring Harbor New York, N.Y.; Cold Spring Harbor Laboratory) or another promoter (see possibility A).

2.3) Possibility C)
an activation sequence
containing at least one Lac operator binding sequence (nucleotide sequence: 5'-GAATTGTGAGCGCTCACAATTC-3') (SEQ ID NO.: 3) for the lac I repressor protein (Fuerst et al., PNAS USA 86, 2549 (1989); Simons et al., PNAS USA 81, 1624 (1984)) and (to whose 3' end) is added
the basal promoter of SV40 (nucleotides 48 to 5191; Tooze (ed) DNA Tumor Viruses (Cold Spring Harbor New York, N.Y., Cold Spring Harbor Laboratory) or another promoter (see possibility A) is added.

2.4) Possibility D)
an activation sequence containing at least one tetracycline operator (tet 0) binding sequence (nucleotide sequence: 5'-TCGAGTTTACCACTCCCTATCAGTGAT AGAGAAAAGTGAAAG-3') (SEQ ID NO.: 4) for the tetracycline repressor (tet R) protein and (to whose 3' end) is added
the basal promoter of SV40 (nucleotides 48 to 5191; Tooze (ed.) DNA Tumor Viruses (Cold Spring Harbor New York, N.Y., Cold Spring Harbor Laboratory) or another promoter (see possibility A).

2.5) Possibility E)
an activation sequence
containing at least one binding sequence [nucleotide sequence: 5'-TAATGATGGCG3'] (SEQ ID NO.: 5) for the ZFHD-1 protein (Pomerantz et al., Science 267, 93 (1995)) and (to whose 3' end) is added
the basal promoter of SV40 (nucleotides 48 to 5191; Tooze (ed.), DNA Tumor Viruses (Cold Spring Harbor New York, N.Y., Cold Spring Harbor Laboratory) or another promoter (see possibility A).

IV. Features of Embodiment B)
1) The Activation Sequence of Promoter Unit I [Component a')]
1.1) The DNA-binding Sequence for a Regulatory Protein [Component $a_1$)]
These sequences include the DNA-binding sequences for transcription factors whose ability to bind DNA is impeded by mutation or which are quantitatively increased or decreased in the cell. Transcription factors and their alterations have been reviewed, for example, by Nichols et al., Blood 80, 2953 (1992); Crepieux et al., Crit. Rev. Oncogen. 5, 615 (1994); LaThangue, TIBS 19, 108 (1994); Lipton, Nature Med. 3, 20 (1997)).

These DNA-binding sequences include, for example, at least one DNA-binding sequence
for the p53 protein [ATAATTGGGCAAGTCTAGGAA-3; (SEQ ID NO.: 6) Kern et al., Science 252, 1708 (1991), Cho et al., Science 265, 346 (1994) or (SEQ ID NO: 16)-(G/A)-(G/A)-(G/A)-C-(A/T)-(T/A)-G; (SEQ ID NO: 15) Cho et al., Science 265, 346 (1994)]
for the Wt-1 protein (Wang et al., Oncogene 10, 415 (1995); Borel et al., Biochem. 35/37, 12070 (1996))
for the NF kappa B protein (nucleotide sequence 5'-GGGACTTTCC-3' (SEQ ID NO.: 7); Urban et al., Genes and Developm. 4, 1975 (1990); Wrong et al., Virol. 189, 750 (1992)) or HIV-LTR (Gimble et al., J. Virol. 62, 4104 (1988))
for the E2F/DP-1 complex (at least one nucleotide sequence 5'-TTCCCGCCAAAA (SEQ ID No.: 8); or 5'-TTTTCCCGCCTTTTTT (SEQ ID NO.: 9) or 5'-TTTTCCCGCGC TTTTTT) (SEQ ID NO.: 10) (Ouellete et al., Oncogene 7, 1075 (1992))
for the Myc/Max protein (at least one nucleotide sequence of 5'-CACGTG-3') (Walhout et al., Nucl. Acids Res. 25, 1493 (1997); Nozaki et al., J. Biochem. 121, 550 (1997)) or of 5'-CATGTG-3' (Fisher et al., EMBO J. 12, 5075 (1993))

1.2) The Basal Promoter [Component $a_2$)]
Examples of these basal promoters are:
the basal promoter of SV40 (nucleotides 48 to 5191; Tooze (ed), DNA Tumor Viruses (Cold Spring Harbor New York, N.Y., Cold Spring Harbor Laboratory) or
the promoter of c-fos (Das et al., Nature 374, 657 (1995)) or
the U2 sn RNA promoter or
the promoter of HSV TK (Papavassiliou et al., J. Biol. Chem. 265, 9402 (1990); Park et al., Mol. Endocrin. 7, 319 (1993))

2) The Repressor [Component b')]
Examples of these repressors are
the lac repressor (Brown et al., Cell 49, 603 (1987); Fürst et al., PNAS USA 86, 2549 (1989)) or
the tetracycline repressor (Gossen et al., PNAS USA 89, 5549 (1992);
Dingermann et al., EMBO J. 11, 1487 (1992))

3) The Activation Sequence [Component $c_1$)] influenced by component b')
These activation sequences include, for example, all the activation sequences which are subsequently listed in section V).

4) The DNA-binding Sequence for the Repressor [Component $c_2$)]
Examples of these DNA-binding sequences are:
at least one Lac operator binding sequence (nucleotide sequence: 5'-GAATTGTGAGCGCTCACAATTC-3') (SEQ ID NO.: 3) for the lac I repressor protein (Fürst et al., PNAS USA 86, 2549 (1989); Simons et al., PNAS USA 81, 1624 (1984)) or
at least one tetracycline operator (tet O) binding sequence (nucleotide sequence:
5'-TCGAGTTTACCACTCCCTATCAGTGATAGAGA AAAGTGAAAG-3') (SEQ ID NO.: 4) for the tetracycline repressor (tet R) protein.

V. Activation Sequence I [Component a) in Embodiment A) and Component $c_1$) in Embodiment B)]
Within the meaning of the invention, nucleotide sequences which, after binding transcription factors, activate the transcription of a gene which is located adjacently at the 3' end are to be used as activation sequences. The choice of the activation sequence depends on the disease to be treated and on the target cell to be transduced. Thus, it is possible for the activation sequence [component a)] to be activated in an unrestricted manner, target cell-specifically, under particular metabolic conditions, cell cycle-specifically or virus-specifically. These promoter sequences have already been described in detail in Patent Applications EP95930524.4, EP95931933.6, EP95931204.2, EP95931205.9, EP97101507.8, EP97102547.3, DE19639103.2 and DE19651443.6. The following are examples of the promoter sequences to be selected:

1) Activator Sequences and Promoters Which can be Activated in an Unrestricted Manner, Such as
   the promoter of RNA polymerase III
   the promoter of RNA polymerase II
   the CMV promoter and CMV enhancer
   the SV40 promoter
2) Viral Promoter and Activator Sequences, Such as
   HBV
   HCV
   HSV
   HPV
   EBV
   HTLV
   HIV When the HIV promoter is used, the entire LTR sequence, including the TAR sequence [position -453 to -80, Rosen et al., Cell 41, 813 (1985)], is to be employed as a virus-specific promoter.

3) Metabolically Activatable Promoter and Enhancer Sequences, Such as the Enhancer Which can be Induced by Hypoxia 4) Cell Cycle-specifically Activatable Promoters Examples of these are the promoter of the cdc25C gene, of the cyclin A gene, of the cdc2 gene, of the B-myb gene, of the DHFR gene, of the E2F-1 gene or of the cdc25B gene, or else binding sequences for transcription factors which appear or are activated during cell proliferation. These binding sequences include, for example, binding sequences for c-myc proteins. These binding sequences also include monomers or multimers of the nucleotide sequence termed the Myc E box [5'-GGAAGCAGACCACGTGGTCTGCTTCC-3' (SEQ ID NO.: 11); Blackwood and Eisenmann, Science 251: 1211 (1991)].

5) Tetracycline-activatable Promoters, Such as the Tetracycline Operator in Combination With a Corresponding Repressor 6) Chimeric Promoters A chimeric promoter is the combination of an upstream activator sequence which can be activated cell-specifically, metabolically or virus-specifically and a downstream promoter module which contains the nucleotide sequence CDE-CHR or E2FBS-CHR, to which suppressive proteins bind and are thereby able to inhibit the activation of the upstream activator sequence in the Go and Gi phases of the cell cycle (PCT/GB94/17366; Lucibello et al., EMBO J. 14, 12 (1994)).

7) Promoters Which Can be Activated Cell-specifically

These preferably include promoters or activator sequences from promoters or enhancers of those genes which encode proteins which are preferentially formed in selected cells.

For example, within the meaning of the invention, promoters for the following proteins are preferably to be used in the following cells:

7.1) Promoter and Activator Sequences Which are Activated in Endothelial Cells
   brain-specific, endothelial glucose-1 transporter
   endoglin
   VEGF receptor 1 (flt-1)
   VEGF receptor 2 (flk-1, KDR)
   tie-1 or tie-2
   B61 receptor (Eck receptor)
   B61
   endothelin, especially endothelin B or endothelin 1
   endothelin receptors, in particular the endothelin B receptor
   mannose 6-phosphate receptors
   von Willebrand factor
   IL-1α, IL-1β
   IL-1 receptor
   vascular cell adhesion molecule (VCAM-1)
   synthetic activator sequences As an alternative to natural endothelial cell-specific promoters, use can also be made of synthetic activator sequences which comprise oligomerized binding sites for transcription factors which are preferentially or selectively active in endothelial cells. An example is the transcription factor GATA-2, whose binding site in the endothelin 1 gene is 5'-TTATCT-3' [Lee et al., Biol. Chem. 266, 16188 (1991), Dorfmann et al., J. Biol. Chem. 267, 1279 (1992) and Wilson et al., Mol. Cell Biol. 10, 4854 (1990)].

7.2) Promoters or Activator Sequences Which are Activated in Cells in the Vicinity of Activated Endothelial Cells
   VEGF The gene regulatory sequences for the VEGF gene are the 5'-flanking region, the 3' flanking region, the c-Src gene or the v-Src gene Steroid hormone receptors and their promoter elements (Truss and Beato, Endocr. Rev. 14, 459 (1993)), in particular the mouse mammary tumor virus promoter 7.3) Promotors or Activator Sequences Which are Activated in Muscle Cells, in Particular Smooth Muscle Cells
   tropomyosin
   α-actin
   α-myosin
   receptor for PDGF
   receptor for FGF
   MRF-4
   phosphofructokinase A
   phosphoglycerate mutase
   troponin C
   myogenin
   receptors for endothelin A
   desmin
   VEGF The gene regulatory sequences for the VEGF gene have already been listed in the section "Promoters which are activated in cells in the vicinity of activated endothelial cells" (see above)

"artificial" promoters

Factors of the Helix-Loop-Helix (HLH) family (MyoD, Myf-5, myogenin, MRF4) are reported to be muscle-specific transcription factors. The zinc finger protein GATA-4 is also a muscle-specific transcription factor. The HLH proteins and also GATA-4 exhibit muscle-specific transcription not only with promoters of muscle-specific genes but also in a heterologous context, for example with artificial promoters as well. Examples of such artificial promoters are multiple copies of the (DNA) binding site for muscle-specific HLH proteins, such as the E box (Myo D) (e.g. 4×AGCAGGTGTTGGGAGGC) or multiple copies of the DNA binding site for GATA-4 of the α-myosin heavy chain gene (e.g. 5'-GGCCGATGGGCA
GATAGAGGGGGCCGAT-GGGCAGATAGAGG3') (SEQ
ID NO.: 12).

7.4) Promoters and Activator Sequences Which are Activated in Glia Cells

These include, in particular, the gene regulatory sequences or elements from genes which encode the following proteins, for example:

the Schwann cell-specific protein Periaxin
glutamine synthetase
the glia cell-specific protein (glial fibrillary acid protein= GFAP)
the glia cell protein S100b
IL-6 (CNTF)
5-HT receptors
TNFα
IL-10
insulin-like growth factor receptors I and II
VEGF The gene regulatory sequences for the VEGF gene have already been listed above.

7.5) Promoters and Activator Sequences Which are Activated in Hematoopoietic Cells Gene regulatory sequences of this nature include promoter sequences for genes for a cytokine or its receptor which are expressed in hematopoietic cells or in adjacent cells, such as the stroma.

These include promoter sequences for the following cytokines and their receptors, for example:

stem cell factor receptor
stem cell factor
IL-1α
IL-1 receptor
IL-3
IL-3 receptor (α-subunit)
IL-3 receptor (β-subunit)
IL-6
IL-6 receptor
GM-CSF
GM-CSF receptor (α-chain)
interferon regulatory factor 1 (IRF-1)
The promoter of IRF-1 is activated equally well by IL-6 as by IFNγ or IFNβ
erythropoietin
erythropoietin receptor.

7.6) Promoters and Activator Sequences which are Activated in Lymphocytes and/or Macrophages These include, for example, the promoter and activator sequences of the genes for cytokines, cytokine receptors and adhesion molecules and receptors for the Fc fragment of antibodies.

Examples are:

IL-1 receptor
IL-1α
IL-1β
IL-2
IL-2 receptor
IL-3
IL-3 receptor (α-subunit)
IL-3 receptor (β-subunit)
IL-4

IL-4 receptor
IL-5
IL-6
IL-6 receptor
interferon regulatory factor 1 (IRF-1) (The promoter of IRF-1 is activated equally well by IL-6 as by IFNγ or IFNβ).
IFNγ-responsive promoter
IL-7
IL-8
IL-10
IFNγ
GM-CSF
GM-CSF receptor (α-chain)
IL-13
LIF
macrophage colony stimulating factor (M-CSF) receptor
type I and II macrophage scavenger receptors
MAC-1 (leukocyte function antigen)
LFA-1α (leukocyte function antigen)
p150,95 (leukocyte function antigen)

7.7) Promoter and Activator Sequences Which are Activated in Synovial Cells

These include the promoter sequences for matrix metalloproteinases (MMP), for example for:

MMP-1 (interstitial collagenase)
MMP-3 (stromelysin/transin)

They further include the promoter sequences for tissue inhibitors of metalloproteinases (TIMP), for example

TIMP-1
TIMP-2
TIMP-3

7.8) Promoter and Activator Sequences Which are Activated in Leukemia Cells

Examples of these are promoters for c-myc
HSP-70
bcl-1/cyclin D-1
bcl-2
IL-6
IL-10
TNFα, TNFβ
HOX-11
BCR-Abl
E2A-PBX-1
PML-RARA (promyelocytic leukemia—retinoic acid receptor)
c-myc
c-myc proteins bind to, and activate, multimers of the nucleotide sequence termed the Myc E box (5'-GGAAGCAGACCAGCTGGTCT GCTTCC-3') (SEQ ID NO.: 11)

7.9) Promoters or Activator Sequences Which are Activated in Tumor Cells

A gene regulatory nucleotide sequence with which transcription factors which are formed or are active in tumor cells interact is envisaged as the promoter or activator sequence.

Within the meaning of this invention, the preferred promoters or activator sequences include gene regulatory sequences or elements from genes which encode proteins which are formed, in particular, in cancer cells or sarcoma cells. Thus, use is preferably made of the promoter of N-CAM protein in the case of small-cell bronchial carcinomas, of the promoter of the hepatitis growth factor receptor or of L-plastin in the case of ovarian carcinomas, and of the promoter of L-plastin or of polymorphic epithelial mucins (PEM) in the case of pancreatic carcinomas.

VI. The Effector Gene (Component d)

Within the meaning of the invention, the effector genes [component d)] encode an active compound for the prophylaxis and/or therapy of a disease. Effector genes and promoter sequences are to be selected with regard to the nature of the therapy of the disease and taking into account the target cells to be transduced.

For example, the following combinations of promoter sequences and effector genes are to be chosen in the case of the following diseases (a detailed description has already been given in Patent Applications EP 95930524.4, EP 95931933.6, EP 95931204.2, EP 95931205.9, EP 97101507.8, DE 19617851.7, DE 19639103.2 and DE 19651443.6, which are hereby incorporated by reference).

1) Therapy of Tumors 1.1) Target Cells proliferating endothelial cells or stroma cells and muscle cells which are adjacent to the endothelial cell, or tumor cells or leukemia cells 1.2) Promoters endothelial cell-specific and cell cycle-specific or cell-nonspecific or muscle cell-specific and cell cycle-specific or tumor cell-specific (solid tumors, leukemia) and cell cycle-specific 1.3) Effector Genes for Inhibitors of Cell Proliferation, for Example for the retinoblastoma protein (pRb=p110) or the related p107 and p130 proteins The retinoblastoma protein (pRb/p110) and the related p107 and p130 proteins are inactivated by phosphorylation. Preference is given to using those genes of these cell cycle inhibitors which exhibit mutations for the inactivation sites of the expressed proteins without the function of the latter thereby being impaired. Examples of these mutations have been described for p110.

The DNA sequence for the p107 protein or the p130 protein is mutated in an analogous manner.

the p53 protein

The protein p53 is inactivated in the cell either by binding to special proteins, such as MDM2, or by the p53 being oligomerized by way of the dephosphorylated C-terminal serine. Consequently, preference is given to using a DNA sequence for a p53 protein which is truncated C-terminally by the serine 392 p21 (WAF-1)

p16 protein other cdk inhibitors the GADD45 protein the bak protein a binding protein for a regulatory protein (see II1.)

1.4) Effector Genes for Coagulation-inducing Factors and Angiogenesis Inhibitors, for Example plasminogen activator inhibitor 1 (PAI-1)

PAI-2

PAI-3 angiostatin interferons (IFNα, IFNα or IFNγ)

platelet factor 4

TIMP-1

TIMP-2

TIMP-3 leukemia inhibitory factor (LIF)

tissue factor (TF) and its coagulation-active fragments 1.5) Effector Genes for Cytostatic and Cytotoxic Proteins, for Example for perforin granzyme

IL-2

IL-4

IL-12 interferons, such as IFN-α, IFNβ or IFNγ

TNF, such as TNFα or TNFβ oncostatin M sphingomyelinase magainin and magainin derivatives 1.6) Effector Genes for Cytostatic or Cytotoxic Antibodies and for Fusion Proteins Between Antigen-binding Antibody Fragments and Cytostatic, Cytotoxic or Inflammatory Proteins or Enzymes The cytostatic or cytotoxic antibodies include those which are directed against membrane structures of endothelial cells, as have been described, for example, by Burrows et al., Pharmac. Ther. 64, 155 (1994), Hughes et al., Cancer Res. 49, 6214 (1989) and Maruyama et al., PNAS USA 87, 5744 (1990). They particularly include antibodies against the VEGF receptors.

They also include cytostatic or cytotoxic antibodies which are directed against membrane structures on tumor cells. Antibodies of this nature have been reviewed, for example, by Sedlacek et al., Contrib. to Oncol. 32, Karger Verlag, Munich (1988) and Contrib. to Oncol. 43, Karger Verlag, Munich (1992). Other examples are antibodies against Sialyl Lewis; against peptides on tumors which are recognized by T cells; against proteins expressed by oncogenes; against gangliosides such as GD3, GD2, GM2, 9-0-acetyl GD3 and fucosyl GM1; against blood group antigens and their precursors; against antigens on polymorphic epithelial mucin; and against antigens on heat shock proteins.

They furthermore include antibodies which are directed against membrane structures of leukemia cells. A large number of monoclonal antibodies of this nature have already been described for diagnostic and therapeutic methods (reviews in Kristensen, Danish Medical Bulletin 41, 52 (1994); Schranz, Therapia Hungarica 38, 3 (1990); Drexler et al., Leuk. Res. 10, 279 (1986); Naeim, Dis. Markers 7, 1 (1989); Stickney et al., Curr. Opin. Oncol. 4, 847 (1992); Drexler et al., Blut 57, 327 (1988); Freedman et al., Cancer Invest. 9, 69 (1991)). Depending on the type of leukemia, monoclonal antibodies, or their antigen-binding antibody fragments, which are directed against the following membrane antigens are suitable, for example, for use as ligands:

| Cells | Membrane antigen |
|---|---|
| AML | CD13 |
|  | CD15 |
|  | CD33 |
|  | CAMAL |
|  | sialosyl-Le |
| B-CLL | CD5 |
|  | CD1c |
|  | CD23 |
|  | idiotypes and isotypes of the membrane immunoglobulins |
| T-CLL | CD33 |
|  | M38 |
|  | IL-2 receptors |
|  | T cell receptors |
| ALL | CALLA |
|  | CD19 |
|  | non-Hodgkin's lymphoma |

The humanization of murine antibodies and the preparation and optimization of the genes for Fab and rec. Fv fragments are effected in accordance with the technique known to the skilled person. The fusion of the rec. Fv fragments with genes for cytostatic, cytotoxic or inflammatory proteins or enzymes is likewise effected in accordance with the state of the art known to the skilled person.

1.7) Effector Genes for Fusion Proteins Comprising Target Cell-binding Ligands and Cytostatic and Cytotoxic Proteins. The Ligands Include all Substances Which Bind to Membrane Structures or Membrane Receptors on Endothelial Cells. Examples are Cytokines such as IL-1 or growth factors or their fragments or part sequences thereof which bind to receptors which are expressed by endothelial cells, for example PDGF, bFGF, VEGF and TGF.

They also include adhesion molecules which bind to activated and/or proliferating endothelial cells. Examples of these are SLex, LFA-1, MAC-1, LECAM-1, $V_L A$-4 or vitronectin.

They furthermore include substances which bind to membrane structures or membrane receptors of tumor or leukemia cells. Examples are hormones or growth factors or their fragments or part sequences thereof which bind to receptors which are expressed by leukemia cells or tumor cells.

Growth factors of this nature have already been described (reviews in Cross et al., *Cell* 64, 271 (1991), Aulitzky et al., *Drugs* 48, 667 (1994), Moore, *Clin. Cancer Res.* 1, 3 (1995), Van Kooten et al., *Leuk. Lymph.* 12, 27 (1993)).

The genes of these ligands which bind to the target cell are fused to cytostatic, cytotoxic or inflammatory proteins or enzymes in accordance with the state of the art using the methods which are known to the skilled person.

1.8) Effector Genes for Inflammation Inducers, for Example for

IL-1

IL-2

RANTES (MCP-2)

monocyte chemotactic and activating factor (MCAF)

IL-8 macrophage inflammatory protein-1 (MIP-1α, -β)

neutrophil activating protein-2 (NAP-2)

IL-3

IL-5 human leukemia inhibitory factor (LIF)

IL-7

IL-11

IL-13

GM-CSF

G-CSF

M-CSF cobra venom factor (CVF) or part sequences of CVF which correspond functionally to human complement factor C3b, i.e. which are able to bind to complement factor B and which, after cleavage by factor D, constitute a C3 convertase human complement factor C3 or its part sequence C3b cleavage products of human complement factor C3 which resemble CVF functionally and structurally bacterial proteins which activate complement or induce inflammations, such as *Salmonella typhimurium* porins, *Staphylococcus aureus* clumping factors, modulins, particularly Gram-negative bacterial modulins, major outer membrane protein of Legionellas or of *Haemophilus influenzae* type B or of Klebsiellas, or M molecules of group G Streptococci.

1.9) Effector Genes for Enzymes for Activating Precursors of Cytostatic Agents, for Example for Enzymes Which Cleave Inactive Precursors (Prodrugs) into Active Cytostatic Agents (Drugs).

Substances of this nature, and the prodrugs and drugs which are in each case affiliated with them, have already been reviewed by Deonarain et al., *Br. J. Cancer* 70, 786 (1994), Mullen, *Pharmac. Ther.* 63, 199 (1994) and Harris et al., *Gene Ther.* 1, 170 (1994). For example, use is to be made of the DNA sequence for one of the following enzymes:

herpes simplex virus thymidine kinase varicella zoster virus thymidine kinase bacterial nitroreductase bacterial β-glucuronidase plant β-glucuronidase from Secale cereale human β-glucuronidase human carboxypeptidase (CB), for example mast cell CB-A, pancreatic CB-B or bacterial carboxypeptidase bacterial β-lactamase bacterial cytosine deaminase human catalase or peroxidase phosphatase, in particular human alkaline phosphatase, human acid prostate phosphatase or type 5 acid phosphatase oxidase, in particular human lysyl oxidase or human acid D-amino oxidase peroxidase, in particular human glutathione peroxidase, human eosinophil peroxidase or human thyroid peroxidase galactosidase 2) Therapy of Autoimmune Diseases and Inflammations 2.1) Target Cells proliferating endothelial cells or macrophages and/or lymphocytes or synovial cells 2.2) Promoters endothelial cell-specific and cell cycle-specific or macrophage- and/or lymphocyte-specific and/or cell cycle-specific or synovial cell-specific and/or cell cycle-specific 2.3) Effector Genes for the Therapy of Allergies, for Example for

IFNβ

IFNγ

IL-10 antibodies or antibody fragments against IL-4 soluble IL-4 receptors

IL-12

TGFβ

2.4) Effector Genes for Preventing the Rejection of Transplanted Organs, for Example for

IL-10

TGFβ soluble IL-1 receptors soluble IL-2 receptors

IL-1 receptor antagonists soluble IL-6 receptors immunosuppressive antibodies or their $V_H$- and $V_L$-containing fragments or their $V_H$ and $V_L$ fragments which are linked by way of a linker. Examples of immunosuppressive antibodies are antibodies which are specific for the T cell receptor or its CD3 complex, or which are directed against CD4 or CD8 or, in addition, against the IL-2 receptor, the IL-1 receptor or the IL-4 receptor, or against the adhesion molecules CD2, LFA-1, CD28 or CD40

2.5) Effector Genes for the Therapy of Antibody-mediated Autoimmune Diseases, for Example for

TGFβ

IFNα

IFNβ

IFNγ

IL-12 soluble IL-4 receptors soluble IL-6 receptors immunosuppressive antibodies or their $V_H$- and $V_L$-containing fragments 2.6) Effector Genes for the Therapy of Cell-mediated Autoimmune Diseases, for Example for

IL-6

IL-9

IL-10

IL-13

TNFα or TNFβ an immunosuppressive antibody or its $V_H$- and $V_L$-containing fragments 2.7) Effector Genes for Inhibitors of Cell Proliferation, Cytostatic or Cytotoxic Proteins and Enzymes for Activating Precursors of Cytostatic Agents Examples of genes which encode proteins of this nature have already been listed in the "Effector genes for the therapy of tumors" section.

In the same form as already described in that section, use can be made, within the meaning of the invention, of effector genes which encode fusion proteins which are composed of antibodies or Fab or rec. Fv fragments of these antibodies, or other ligands which are specific for the target cell, and the abovementioned cytokines, growth factors, receptors, cytostatic or cytotoxic proteins and enzymes.

2.8) Effector Genes for the Therapy of Arthritis

Within the meaning of the invention, effector genes are selected whose expressed protein directly or indirectly inhibits inflammation, for example in a joint, and/or promotes the reconstitution of extracellular matrix (cartilage, connective tissue) in a joint.

Examples are

IL-1 receptor antagonist (IL-1 RA);

IL-1 RA inhibits the binding of IL-1α, β soluble IL-1 receptor;

soluble IL-1 receptor binds and inactivates IL-1

IL-6

IL-6 increases the secretion of TIMP and superoxides and decreases the secretion of IL-I and TNFα by synovial cells and chondrocytes soluble TNF receptor soluble TNF receptor binds and inactivates TNF.

IL-4

IL-4 inhibits the formation and secretion of IL-1, TNFα and MMP

IL-10

IL-10 inhibits the formation and secretion of IL-1, TNF α and MMP and increases the secretion of TIMP insulin-like growth factor (IGF-1) IGF-1 stimulates the synthesis of extracellular matrix.

TGFβ, especially TGFβ1 and TGFβ2 TGFβ stimulates the synthesis of extracellular matrix.

superoxide dismutase

TIMP, especially TIMP-1, TIMP-2 or TIMP-3

3) Therapy of Deficient Hematopoiesis 3.1) Target Cells proliferating, immature cells of the hematopoietic system or stroma cells which are adjacent to the hematopoietic cells 3.2) Promoters specific for hematopoietic cells and/or cell cycle-specific cell-nonspecific and cell cycle-specific 3.3) Effector Genes for the Therapy of Anemia, for Example for erythropoietin 3.4) Effector Genes for the Therapy of Leukopenia, for Example for

G-CSF

GM-CSF

M-CSF 3.5) Effector Genes for the Therapy of Thrombocytopenia, for Example for

IL-3 leukemia inhibitory factor (LIF)

IL-11 thrombopoietin

4) Therapy of Damage to the Nervous System 4.1) Target Cells glia cells or proliferating endothelial cells 4.2) Promoters glia cell-specific and cell cycle-specific or endothelial cell-specific and cell cycle-specific or nonspecific and cell cycle-specific 4.3) Effector Genes for Neuronal Growth Factors, for Example

FGF nerve growth factor (NGF)

brain-derived neurotrophic factor (BDNF)

neurotrophin 3 (NT-3)

neurotrophin 4 (NT-4)

ciliary neurotrophic factor (CNTF)

4.4) Effector Genes for Enzymes, for Example for tyrosine hydroxylase dopa decarboxylase 4.5) Effector Genes for Cytokines and Their Inhibitors Which Inhibit or Neutralize the Neurotoxic Effect of TNFα, for Example for

TGFβ soluble TNF receptors

TNF receptors neutralise TNFα

IL-10

IL-10 inhibits the formation of IFNγ, TNFα, IL-2 and IL-4 soluble IL-1 receptors

IL-I receptor I

IL-I receptor II soluble IL-1 receptors neutralize the activity of IL-1

IL-1 receptor antagonist soluble IL-6 receptors

5) Therapy of Disturbances of the Blood Coagulation and Blood Circulation System 5.1) Target cells endothelial cells or proliferating endothelial cells or somatic cells in the vicinity of endothelial cells and smooth muscle cells or macrophages 5.2) Promoters cell-nonspecific and cell cycle-specific or specific for endothelial cells, smooth muscle cells or macrophages and cell cycle-specific 5.3) Structural Genes for the Inhibition of Coagulation or for the Promotion of Fibrinolysis, for Example for tissue plasminogen activator (tPA)

urokinase-type plasminogen activator (uPA)

hybrids of tPA and uPA protein C hirudin serine proteinase inhibitors (serpins), such as C-1S inhibitor, α1-antitrypsin or antithrombin III tissue factor pathway inhibitor (TFPI)

5.4) Effector Genes for Promoting Coagulation, for Example for

F VIII

F IX von Willebrand factor

F XIII

PAI-I

PAI-2 tissue factor and fragments thereof 5.5) Effector Genes for Angiogenesis Factors, for Example for

VEGF

FGF 5.6) Effector Genes for Lowering the Blood Pressure, for Example for kallikrein endothelial cell nitric oxide synthase 5.7) Effector Genes for Inhibiting the Proliferation of Smooth Muscle Cells Following Injury to the Endothelial Layer, for Example for an antiproliferative, cytostatic or cytotoxic protein or an enzyme for cleaving precursors of cytostatic agents into cytostatic agents, as have already been listed above (under tumor) or a fusion protein of one of these active compounds with a ligand, for example an antibody or antibody fragments which is/are specific for muscle cells 5.8) Effector Genes for Other Blood Plasma Proteins, for Example for albumin C1 inactivator serum cholinesterase transferrin antritrypsin 5.9) Effector Genes for Antibacterial Proteins The antibacterial proteins include, for example, antibodies which neutralize bacterial toxins or opsonize bacteria. Examples are antibodies against:

Meningococci C or B

*E. coli*

Borrelia

Pseudomonas

Helicobacter pylori

Staphylococcus aureus

6) Vaccinations 6.1) Target Cells muscle cells or macrophages and/or lymphocytes endothelial cells 6.2) Promoters nonspecific and cell cycle-specific or target cell-specific and cell cycle-specific 6.3) Effector Genes for the Prophylaxis of Infectious Diseases The possibilities of preparing effective vaccines conventionally are limited. The technology of DNA vaccines was therefore developed. However, these DNA vaccines raise questions with regard to efficacy. The DNA vaccine which is prepared in accordance with this invention can be expected to be more effective. The active substance to be selected is the DNA for a protein which is formed by the infectious agent and which leads, by means of inducing an immune reaction, i.e. by means of antibody formation and/or by means of cytotoxic T lymphocytes, to the neutralization and/or destruction of the pathogen. So-called neutralization antigens of this nature are already employed as vaccination antigens (see review in Ellis, *Adv. Exp. Med. Biol.* 327, 263 (1992)).

Within the meaning of the invention, preference is given to the DNA which encodes neutralization antigens of the following pathogens:

influenza A virus

HIV rabies virus

HSV (herpes simplex virus)

RSV (respiratory syncytial virus)

parainfluenza virus rotavirus

VZV (varicella zoster virus)

CMV (cytomegalovirus)
measles virus
HPV (human papilloma virus)
HBV (hepatitis B virus)
HCV (hepatitis C virus)
HDV (hepatitis D virus)
HEV (hepatitis E virus)
HAV (hepatitis A virus)
*Vibrio cholerae* antigen
*Borrelia burgdorferi*
*Helicobacter pylori*
malaria antigen However, within the meaning of the invention, active substances of this nature also include the DNA for an antiidiotype antibody or its antigen-binding fragments whose antigen-binding structures (the complementarity determining regions) constitute copies of the protein or carbohydrate structure of the neutralization antigen of the infectious agent.

Antiidiotype antibodies of this nature can, in particular, replace carbohydrate antigens in the case of bacterial infectious agents. Antiidiotype antibodies of this nature and their cleavage products have been reviewed by Hawkins et al., *J. Immunother.* 14, 273 (1993) and Westerink and Apicella, Springer Seminars in *Immunopathol.* 15, 227 (1993).

6.4) Effector Genes for "Tumor Vaccines"

These include antigens on tumor cells. Antigens of this nature have been reviewed, for example, by Sedlacek et al., *Contrib. to Oncol.* 32, Karger Verlag, Munich (1988) and *Contrib. to Oncol.* 43, Karger Verlag, Munich (1992).

Other examples are the genes for the following protein antigens or for the variable region ($V_L$, $V_H$) of antiidiotype antibodies which correspond to the following non-protein antigens:

gangliosides
sialyl Lewis
peptides on tumors which are recognized by T cells
proteins which are expressed by oncogenes
blood group antigens and their precursors
antigens on tumor-associated mucin
antigens on heat shock proteins 7) The Therapy of Chronic Infectious Diseases
7.1) Target Cell
liver cell
lymphocyte and/or macrophage
epithelial cell
endothelial cell
7.2) Promoters
virus-specific or cell-specific and cell cycle-specific
7.3) Effector Genes, for Example for
a protein which exhibits cytostatic, apoptotic or cytotoxic effects.
an enzyme which cleaves a precursor of an antiviral or cytotoxic substance into the active substance.
7.4) Effector Genes for Antiviral Proteins
cytokines and growth factors which have an antiviral effect. These include, for example, IFNα, IFNβ, IFN-γ, TNFβ, TNFα, IL-1 or TGFβ
antibodies of a specificity which inactivates the respective virus, or their $V_H$- and $V_L$-containing fragments, or their $V_H$ und $V_L$ fragments which are linked by way of a linker, and which are prepared as already described.

The following are examples of antibodies against virus antigens:
anti-HBV
anti-HCV
anti-HSV
anti-HPV
anti-HIV
anti-EBV
anti-HTLV
anti-Coxsackie virus
anti-Hantaan virus
a Rev-binding protein. These proteins bind to the Rev RNA and inhibit Rev-dependent posttranscriptional steps in retrovirus gene expression.
Examples of Rev-binding proteins are:
RBP9-27
RBP1-8U
RBP1-8D
pseudogenes of RBP1-8
ribozymes which digest the mRNA of genes for cell cycle control proteins or the mRNA of viruses. Ribozymes which are catalytic for HIV have been reviewed, for example, by Christoffersen et al., *J. Med. Chem.* 38, 2033 (1995).

VII. Combination of Identical or Different Effector Genes

The invention furthermore relates to a self-enhancing, where appropriate pharmacologically controllable, expression system in which the DNA sequences of two identical or two different effector genes [component c) and c')] are combined. For the two DNA sequences to be expressed, a further promoter sequence or preferably the cDNA for an "internal ribosome entry site" (IRES) is intercalated, as a regulatory element, between the two effector genes.

An IRES makes it possible to express two DNA sequences which are linked to each other by way of an IRES.

IRES of this nature have been described, for example, by Mountford and Smith, TIG 11, 179 (1995); Kaufman et al., *Nucl. Acids Res.* 19, 4485 (1991); Morgan et al., *Nucl. Acids Res.* 20, 1293 (1992); Dirks et al., *Gene* 128, 247 (1993); Pelletier and Sonenberg, *Nature* 334, 320 (1988) and Sugitomo et al., *BioTechn.* 12, 694 (1994).

Thus, use can be made, for example, of the cDNA for the IRES sequence of poliovirus (position $\leq 140$ to $\geq 630$ of the 5' UTR).

Within the meaning of the invention, effector genes which exhibit an additive effect are preferably to be linked by way of additional promoter sequences or an IRES sequence.

Within the meaning of the invention, the following are examples of preferred combinations of effector genes for:

1) The Therapy of Tumors
    identical or different, cytostatic, apoptotic, cytotoxic or inflammatory proteins or
    identical or different enzymes for cleaving the precursor of a cytostatic agent
2) The Therapy of Autoimmune Diseases
    different cytokines or receptors having a synergistic effect for the inhibition of the cellular and/or humoral immune reaction or
    different or identical TIMPs
3) The Therapy of Deficient Hematopoiesis
    different, hierarchically consecutive cytokines, such as IL-1, IL-3, IL-6 or GM-CSF and erythropoietin, G-CSF or thrombopoietin
4) The Therapy of Nerve Cell Damage
    a neuronal growth factor and a cytokine or the inhibitor of a cytokine 5) The Therapy of Disturbances of the Blood Coagulation and Blood Circulation System an antithrombotic agent and a fibrinolytic agent (e.g. tPA or uPA) or a cytostatic, apoptotic or cytotoxic protein and an antithrombotic agent or a fibrinolytic agent several different blood coagulation factors acting synergistically, for example F VIII and vWF or F VIII and F IX 6) Vaccinations an antigen and an immunostimulatory cytokine, such as IL-1α, IL-1β, IL-2, GM-CSF, IL-3 or IL-4 receptor different antigens of one infectious agent or of different infectious agents or different antigens of one tumor type or of different tumor types 7) Therapy of Viral Infectious Diseases an antiviral protein and a cytostatic, apoptotic or cytotoxic protein antibodies against different surface antigens of one virus or several viruses 8) Therapy of Bacterial Infectious diseases antibodies against different surface antigens and/or toxins of an organism Insertion of signal sequences and transmembrane domains:

1) Enhancing the Translation

In order to enhance the translation, the nucleotide sequence GCCACC (SEQ ID NO: 17) or GCCGCC (Kozak, J., *Cell Biol.* 108, 299 (1989)) can be inserted at the 3' end of the promoter sequence and directly at the 5' end of the start signal (ATG) of the signal or transmembrane sequence.

2) Facilitating Secretion

In order to facilitate secretion of the expression product of the effector gene, the homologous signal sequence which may be present in the DNA sequence of the effector gene can be replaced with a heterologous signal sequence which improves extracellular discharge.

Thus, the immunoglobulin signal sequence (DNA position ≦63 to ≧107; Riechmann et al., *Nature* 332, 323 (1988)) or the CEA signal sequence (DNA position ≦33 to ≧134; Schrewe et al., *Mol. Cell Biol.* 10, 2738 (1990); Berling et al., *Cancer Res.* 50, 6534 (1990)) or the human respiratory syncytial virus glycoprotein signal sequence (cDNA for amino acids ≦38 to ≧50 or 48 to 65; Lichtenstein et al., *J. Gen. Virol.* 77, 109 (1996)) can for example be inserted.

3) Anchoring the Active Compound 3.1) As an alternative or in addition to the signal sequence, a sequence for a transmembrane domain can be inserted for the purpose of anchoring the active compound in the cell membrane of the transduced cell forming the active compound.

Thus, the transmembrane sequence of human macrophage colony-stimulating factor (DNA position <1485 to >1554; Cosman et al., *Behning Inst. Mitt.* 83, 15 (1988)) or the DNA sequence for the signal and transmembrane region of human respiratory syncytial virus (RSV) glycoprotein G (amino acids 1 to 63 or their part sequences, amino acids 38 to 63; Vijaya et al., *Mol. Cell Biol.* 8, 1709 (1988); Lichtenstein et al., *J. Gen. Virol.* 77, 109 (1996)) or the DNA sequence for the signal and transmembrane region of influenza virus neuraminidase (amino acids 7 to 35 or the part sequence amino acids 7 to 27; Brown et al., *J. Virol.* 62, 3824 (1988)) can, for example, be inserted between the promoter sequence and the sequence of the effector gene.

3.2) However, the nucleotide sequence for a glycophospholipid anchor can also be inserted for the purpose of anchoring the active compound in the cell membrane of the transduced cells forming the active compound.

A glycophospholipid anchor is inserted at the 3' end of the nucleotide sequence for the effector gene with it being possible for this insertion to take place in addition to the insertion of a signal sequence.

Glycophospholipid anchors have been described, for example, for CEA, for N-CAM and for other membrane proteins such as Thy-1, (see review in Ferguson et al., *Ann. Rev. Biochem.* 57, 285 (1988)).

3.3) The use of a DNA sequence for a ligand-active compound fusion protein represents another option for anchoring active compounds to the cell membrane in accordance with the present invention. The specificity of the ligand of this fusion protein is directed towards a membrane structure on the cell membrane of the chosen target cell.

The ligands which bind to the surface of cells include, for example, antibodies or antibody fragments which are directed against structures on the surface of, for example:

endothelial cells. These antibodies include, in particular, antibodies against the VEGF receptors or against kinin receptors or of muscle cells, such as antibodies against actin or antibodies against angiotensin II receptors or antibodies against receptors for growth factors, for example against EGF receptors or against PDGF receptors or against FGF receptors or antibodies against endothelin A receptors The ligands also include antibodies or their fragments which are directed against tumor-specific or tumor-associated antigens on the tumor cell membrane. Antibodies of this nature have already been described.

The murine monoclonal antibodies are preferably to be employed in humanized form. Fab and rec. Fv fragments and their fusion products are prepared, as already described, using the technology with which the skilled person is familiar.

The ligands furthermore include all active compounds such as cytokines or adhesion molecules, growth factors or their fragments or part sequences thereof, mediators or peptide hormones which bind to membrane structures or membrane receptors on the particular cell selected. Examples of these ligands are:

ligands for endothelial cells, such as IL-1, PDGF, bFGF, VEGF, TGGβ or kinin and derivatives or analogs of kinin.

In addition, the ligands include adhesion molecules. Adhesion molecules of this nature, such as SLex, LFA-1, MAC-1, LeCAM-1, V$_L$A-4 or vitronectin and derivatives or analogs of vitronectin, have already been described for endothelial cells (reviews in Augustin-Voss et al., *J. Cell Biol.* 119, 483 (1992); Pauli et al., *Cancer Metast. Rev.* 9, 175 (1990); Honn et al., *Cancer Metast. Rev.* 11, 353 (1992); Varner et al., *Cell Adh. Commun.* 3, 367 (1995)).

EXAMPLE

The invention is described in more detail in the following illustrative examples. Although the examples may represent only selected embodiments of the invention, it should be understood that the following examples are illustrative and not limiting.

Example 1

Preparation of an Oncogene-controlled Expression System

The oncogene-controlled expression system according to the invention is composed of the following, different nucleotide sequences which follow each other in a downstream direction:

Component a)
    the promotor of the cdc25C gene (nucleic acids −290 to +121;
Zwicker et al., *EMBO J.* 14, 4514 (1995); Zwicker et al., *Nucl. Acids Res.* 23, 3822 (1995))
Component b)
    the nuclear localization signal (NLS) of SV40 (SV40 large T, amino acids 126 to 132; PKKKRKV (SEQ ID NO.: 13);
Dingwall et al., *TIBS* 16, 478 (1991)
    the acid transactivation domain (TAD) of HSV-1 VP16 (amino acids 406 to 488; Triezenberg et al., *Genes Developm.* 2, 718 (1988); Triezenberg, *Curr. Opin. Gene Developm.* 5, 190 (1995))
    the RB binding sequence of the E2F-1 protein (amino acids 409 to 426 (LDYHFGLEEGEGIRDLFD) (SEQ ID NO.: 14);
Flemington et al., *PNAS USA* 90, 6914 (1993); Helin et al., *Cell* 70, 337 (1992))
    the cDNA for the DNA binding domain of the Gal4 protein (amino acids 1 to 147; Chasman und Kornberg, *Mol. Cell Biol.* 10, 2916 (1990))
Component c)
    10× the binding sequence for the Gal4 DNA-binding sequence having the nucleotide sequence 5'-CGGACAATGTTGACCG-3' (SEQ ID NO.: 1) (Chasman and Kornberg, *Mol. Cell Biol.* 10, 2916 (1990)
    the SV40 basal promoter (nucleic acids 48 to 5191; Toose (ed) DNA Tumor Viruses; Cold Spring Harbor, New York, N.Y., Cold Spring Harbor Laboratory)
Component d)
    the sequence GCCACC (SEQ ID NO: 17) (Kozak, *J. Cell Biol.* 108, 229 (1989))
    the cDNA for the immunoglobulin signal peptide (nucleotide sequence 63 to 107; Riechmann et al., *Nature* 332, 323 (1988))
    the cDNA for β-glucuronidase (nucleotide sequence 93 to 1982;
Oshima et al., *PNAS USA* 84, 685 (1987)

The individual components of the construct are linked by means of suitable restriction sites which are introduced at the termini of the different elements by way of PCR amplification. The linking is effected using enzymes which are specific for the restriction sites, and DNA ligases, which are known to the skilled person. These enzymes can be obtained commercially.

The nucleotide construct which has thus been prepared is cloned into the pXP2 plasmid vector (Nordeen, *BioTechniques* 454 (1988)), which is used for an in-vivo application either directly or in colloidal dispersion systems.

3T3 fibroblasts (RB-positive) and osteosarcoma cells (SAOS-2, RB-negative) which are being maintained in culture are transfected with the above described plasmid using the method known to the skilled person (Lucibello et al., *EMBO J.* 132 (1995)), and the quantity of β-glucuronidase which is produced by the fibroblasts or by the osteosarcoma cells is measured using 4-methylumbelliferyl-β-glucuronide as the substrate.

In order to check the cell cycle specificity, the osteosarcoma cells are synchronized in $G_0/G_1$ by removing methionine for 48 hours. The DNA content of the cells is determined in a fluorescence-activated cell sorter after staining with Hoechst 33258 (L-ucibello et al., *EMBO J.* 132 (1995)).

The following results are obtained:

No increase in β-glucuronidase can be ascertained in transfected fibroblasts (RB-positive) when compared with untransfected fibroblasts.

Transfected osteosarcoma cells (RB-negative) express markedly more β-glucuronidase than do untransfected osteosarcoma cells.

Proliferating osteosarcoma cells (DNA>2S; S=single set of chromosomes) secrete markedly more β-glucuronidase than do osteosarcoma cells which are synchronized in $G_0/G_1$ (DNA=2S).

Consequently, the above described expression system gives rise to an RB-dependent expression of the structural gene β-glucuronidase which can be regulated, for example, in a cell cycle-dependent manner depending on the choice of the promoter sequence.

Example 2

Preparation of a Virus-controlled Expression System

The virus-controlled expression system according to the invention is composed of the following different nucleotide sequences which follow each other in a downstream direction:

Component a)
    the promoter of the cdc25C gene (nucleic acids −290 to +121;
Zwicker et al., *EMBO J.* 14, 4514 (1995); Zwicker et al., *Nucl. Acids Res.* 23, 3822 (1995))
Component b)
    the nuclear localization signal (NLS) of SV40 (SV40 large T, amino acids 126 to 132; PKKKRKV (SEQ ID NO.: 13); Dingwall et al., *TIBS* 16, 478 (1991))
    the acid transactivation domain (TAD) of HSV-1 VP16 (amino acids 406 to 488; Triezenberg et al., *Genes Developm.* 2, 718 (1988); Triezenberg, *Curr. Opin. Gene Developm.* 5, 190 (1995))
    the E6 protein of the HPV-18 virus (nucleotide sequence 100 to 578; Roggenbuck et al., *J. Virol.* 65, 5068 (1991))
    the cDNA for the DNA-binding domain of the Gal4 protein (amino acids 1 to 147; Chasman and Kornberg, *Mol. Cell Biol.* 10, 2916 (1990))
Component c)
    10×the binding sequence for the Gal4 DNA-binding sequence having the nucleotide sequence 5'-CGGACAATGTTGACCG-3' (SEQ ID NO.: 1) (Chasman and Kornberg, *Mol. Cell Biol.* 10, 2916 (1990)
    the SV40 basal promotor (nucleic acids 48 to 5191; Toose (ed) DNA Tumor Viruses; Cold Spring Harbor, New York, N.Y., Cold Spring Harbor Laboratory)
Component d)
    the sequence GCCACC (SEQ ID NO: 17) (Kodak, *J. Cell Biol.* 108, 229 (1989))
    the cDNA for the immunoglobulin signal peptide (nucleotide sequence 63 to 107; Riechmann et al., *Nature* 332, 323 (1988))
    the cDNA for β-glucuronidase (nucleotide sequence 93 to 1982; Oshima et al., *PNAS USA* 84, 685 (1987)

The individual components of the construct are linked by means of suitable restriction sites which are introduced at the termini of the different elements by means of PCR amplification. The linking is effected using enzymes which are specific for the restriction sites, and DNA ligases, known to the skilled person. These enzymes can be obtained commercially.

The nucleotide construct which has thus been prepared is cloned into a pUC18/19 plasmid vector, which is used for an in-vivo application either directly or in colloidal dispersion systems.

Human fibroblasts (Wi-38, E6/E7-negative) and cervical carcinoma cells (HeLa, HPV-18-E6/E7-positive) which are being maintained in culture are transfected with the above described plasmid using the method known to the skilled person (Lucibello et al., *EMBO J.* 132 (1995)) and the quantity of β-glucuronidase which is produced by these cells is measured using 4-methylumbelliferyl-β-glucuronide as a substrate.

In order to check the cell cycle specificity, HeLa cells are synchronized in $G_0/G_1$ by removing methionine for 48 hours. The DNA content of the cells is determined in a fluorescence-activated cell sorter after staining with Hoechst 33258 (Lucibello et al., *EMBO J.* 132 (1995)).

The following results are obtained:

No increase in β-glucuronidase can be ascertained in transfected fibroblasts when compared with untransfected fibroblasts. Transfected HeLa cells express markedly more β-glucuronidase than do untransfected HeLa cells.

Proliferating HeLa cells (DNA>2S; S=single set of chromosomes) secrete markedly more β-glucuronidase than do HeLa cells which are synchronized in $G_0/G_1$ (DNA=2S).

Consequently, the above described expression system gives rise to virus-specific (HPV18) expression of the structural gene β-glucuronidase which can be regulated, for example, in a cell cycle-dependent manner depending on the choice of the promoter sequence.

Following local administration, for example at the site of the tumor, or following intracranial or subarachnoidal administration or systemic, preferably intravenous or intraarterial administration, an active compound according to Examples 1 and 2 ensures that it is mainly, if not exclusively, only those cells which exhibit a mutated oncogene or a virus infection which secrete β-glucuronidase. This β-glucuronidase cleaves a now injected, well-tolerated doxorubicin-β-glucuronide (Jacquesy et al., EP 0 511 917 A1) into the cytostatically acting doxorubicin. The latter inhibits the endothelial cell proliferation and acts cytostatically on these cells and also on adjacent tumor cells. This results in inhibition of the growth of the tumor.

The invention described herein may be embodied in other specific forms without departing from the spirit or essential characteristics thereof. The specific embodiments previously described are therefore to be considered as illustrative of, and not limiting, the scope of the invention. Additionally, the disclosure of all publications and patent applications cited above, including Federal Republic of Germany Application No. 19751587.8, are expressly incorporated herein by reference in their entireties to the same extent as if each were incorporated by reference individually.

We claim:

1. A nucleic acid construct for expressing an effector protein, comprising:
   (a) a first promoter, wherein said first promoter comprises the promoter of the cdc25C gene (nucleic acids −290 to +121);
   (b) a polynucleotide encoding a transcription factor, wherein the expression of the transcription factor is controlled by the first promoter, and wherein said transcription factor comprises the nuclear localization signal (NLS) of SV40 (SV40 large T, amino acids 126 to 132, PKKKRKV (SEQ ID NO: 13), the acid transactivation domain (TAD) of HSV-1 VP16 (amino acids 406 to 488), the RB binding sequence of the E2F-1 protein (amino acids 409 to 426 (LDYHFGLEEGEGIRDLFD) (SEQ ID NO: 14), and the DNA binding domain of the Gal4 protein (amino acids 1 to 147);
   (c) a second promoter, to which the transcription factor binds, wherein said second promoter comprises 10× the binding sequence for the Gal4 DNA-binding sequence having the nucleotide sequence 5'-CGGACAATGTTGACCG-3' (SEQ ID NO: 1) and the SV40 basal promoter (nucleic acids 48 to 5191); and
   (d) a polynucleotide encoding the effector protein, comprising the sequence GCCACC (SEQ ID NO: 17), the cDNA for the immunoglobulin signal peptide (nucleotide sequence 63 to 107) and the cDNA for Θ-glucuronidase (nucleotide sequence 93 to 1982), wherein the expression of the effector protein is controlled by the second promoter, wherein the activity of the transcription factor depends on one or more cellular regulatory proteins that bind to the transcription factor and affect the activity thereof.

2. A nucleic acid construct for expressing an effector protein, comprising:

(a) a first promoter, wherein the first promoter comprises the promoter of the cdc25C gene (nucleic acids −290 to +121);

(b) a polynucleotide encoding a transcription factor, wherein the expression of the transcription factor is controlled by the first promoter, and the transcription factor comprises the nuclear localization signal (NLS) of (SV40 large T, amino acids 126 to 132, PKKKRKV (SEQ ID NO: 13), the acid transactivation domain (TAD) of HSV-1 VP16 (amino acids 406 to 488), the E6 protein of the HPV-18 virus (encoded by nucleotide sequence 100 to 578), and the DNA-binding domain for the Gal4 protein (amino acids 1 to 147);

(c) a second promoter, to which the transcription factor binds, wherein the second promoter comprises 10× the binding sequence for the Gal4 DNA-binding sequence having the nucleotide sequence 5'-CGGACAATGTTGACCG-3' (SEQ ID NO: 1) and the SV40 basal promoter (nucleic acids 48 to 5191); and (d) a polynucleotide encoding the effector protein, comprising the sequence GCCACC (SEQ ID NO: 17), the cDNA for the immunoglobulin signal peptide (nucleotide sequence 63 to 107) and the cDNA for Θ-glucuronidase (nucleotide sequence 93 to 1982) wherein the expression of the effector protein is controlled by the second promoter, wherein the activity of the transcription factor depends on one or more cellular regulatory proteins that bind to the transcription factor and affect the activity thereof.

* * * * *

SEQUENCE LISTING

```
<160> NUMBER OF SEQ ID NOS: 17

<210> SEQ ID NO 1
<211> LENGTH: 17
<212> TYPE: DNA
<213> ORGANISM: Homo sapiens

<400> SEQUENCE: 1
cggacaactg ttgaccg                                                      17

<210> SEQ ID NO 2
<211> LENGTH: 20
<212> TYPE: DNA
<213> ORGANISM: Homo sapiens

<400> SEQUENCE: 2
tactgtatgt acatacagta                                                   20

<210> SEQ ID NO 3
<211> LENGTH: 22
<212> TYPE: DNA
<213> ORGANISM: Homo sapiens

<400> SEQUENCE: 3
gaattgtgag cgctcacaat tc                                                22

<210> SEQ ID NO 4
<211> LENGTH: 42
<212> TYPE: DNA
<213> ORGANISM: Homo sapiens

<400> SEQUENCE: 4
tcgagtttac cactccctat cagtgataga gaaaagtgaa ag                          42

<210> SEQ ID NO 5
<211> LENGTH: 11
<212> TYPE: DNA
```

```
<213> ORGANISM: Homo sapiens

<400> SEQUENCE: 5
taatgatggc g                                                           11

<210> SEQ ID NO 6
<211> LENGTH: 21
<212> TYPE: DNA
<213> ORGANISM: Homo sapiens

<400> SEQUENCE: 6
ataattgggc aagtctagga a                                                21

<210> SEQ ID NO 7
<211> LENGTH: 10
<212> TYPE: DNA
<213> ORGANISM: Homo sapiens

<400> SEQUENCE: 7
gggactttcc                                                             10

<210> SEQ ID NO 8
<211> LENGTH: 14
<212> TYPE: DNA
<213> ORGANISM: Homo sapiens

<400> SEQUENCE: 8
ttttcccgcc aaaa                                                        14

<210> SEQ ID NO 9
<211> LENGTH: 16
<212> TYPE: DNA
<213> ORGANISM: Homo sapiens

<400> SEQUENCE: 9
ttttcccgcc tttttt                                                      16

<210> SEQ ID NO 10
<211> LENGTH: 17
<212> TYPE: DNA
<213> ORGANISM: Homo sapiens

<400> SEQUENCE: 10
ttttcccgcg ctttttt                                                     17

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Promoter

<400> SEQUENCE: 11
ggaagcagac cacgtggtct gcttcc                                           26

<210> SEQ ID NO 12
<211> LENGTH: 41
<212> TYPE: DNA
<213> ORGANISM: Artificial Sequence
<220> FEATURE:
<223> OTHER INFORMATION: Description of Artificial Sequence: Promoter

<400> SEQUENCE: 12
ggccgatggg cagatagagg gggccgatgg gcagatagag g                          41
```

```
<210> SEQ ID NO 13
<211> LENGTH: 7
<212> TYPE: PRT
<213> ORGANISM: Homo sapiens

<400> SEQUENCE: 13

Pro Lys Lys Lys Arg Lys Val
 1               5

<210> SEQ ID NO 14
<211> LENGTH: 18
<212> TYPE: PRT
<213> ORGANISM: Homo sapiens

<400> SEQUENCE: 14

Leu Asp Tyr His Phe Gly Leu Glu Glu Gly Glu Gly Ile Arg Asp Leu
 1               5                  10                  15

Phe Asp

<210> SEQ ID NO 15
<211> LENGTH: 7
<212> TYPE: DNA
<213> ORGANISM: Homo sapiens

<400> SEQUENCE: 15 rrrcwwg                                                                7

<210> SEQ ID NO 16
<211> LENGTH: 68
<212> TYPE: DNA
<213> ORGANISM: Artificial Sequence
<220> FEATURE:
<223> OTHER INFORMATION: Description of Artificial Sequence: Promoter

<400> SEQUENCE: 16
agcaggtgtt gggaggcagc aggtgttggg aggcagcagg tgttgggagg cagcaggtgt    60
tgggaggc                                                              68

<210> SEQ ID NO 17
<211> LENGTH: 6
<212> TYPE: DNA
<213> ORGANISM: Artificial Sequence
<220> FEATURE:
<223> OTHER INFORMATION: Description of Artificial Sequence: Nucleotide

<400> SEQUENCE: 17 gccacc                                                                 6
```